(12) United States Patent
Uemori

(10) Patent No.: US 10,430,944 B2
(45) Date of Patent: Oct. 1, 2019

(54) IMAGE PROCESSING APPARATUS, IMAGE PROCESSING METHOD, AND PROGRAM

(71) Applicant: Sony Corporation, Tokyo (JP)

(72) Inventor: Takeshi Uemori, Tokyo (JP)

(73) Assignee: Sony Corporation, Tokyo (JP)

( * ) Notice: Subject to any disclaimer, the term of this patent is extended or adjusted under 35 U.S.C. 154(b) by 198 days.

(21) Appl. No.: 15/391,064

(22) Filed: Dec. 27, 2016

(65) Prior Publication Data

US 2017/0109884 A1 Apr. 20, 2017

Related U.S. Application Data

(63) Continuation of application No. 14/934,204, filed on Nov. 6, 2015, now Pat. No. 9,569,691, which is a
(Continued)

(30) Foreign Application Priority Data

Apr. 15, 2013 (JP) ................................ 2013-084669

(51) Int. Cl.
*G06K 9/00* (2006.01)
*G06T 7/00* (2017.01)
(Continued)

(52) U.S. Cl.
CPC ............ *G06T 7/0012* (2013.01); *A61B 1/045* (2013.01); *G01B 11/026* (2013.01); *G01B 11/14* (2013.01);
(Continued)

(58) Field of Classification Search
CPC ............. G06K 9/00201; G06K 9/6215; G01B 11/026; G01B 11/14; G06T 7/0075
See application file for complete search history.

(56) References Cited

U.S. PATENT DOCUMENTS 6,163,337 A * 12/2000 Azuma .................. G06T 15/10
348/43
8,233,031 B2 * 7/2012 Saito ........................ G01C 3/08
348/47
(Continued)

FOREIGN PATENT DOCUMENTS

JP 2001-103513 A 4/2001
JP 2012-065851 A 4/2012

*Primary Examiner* — Shefali D Goradia
(74) *Attorney, Agent, or Firm* — Wolf, Greenfield & Sacks, P.C.

(57) ABSTRACT

An image processing apparatus includes an attention area detection unit, a luminance parallax conversion unit, and a parallax estimation unit. The attention area detection unit is configured to detect an attention area including a desired subject from a standard image. The luminance parallax conversion unit is configured to perform a luminance parallax conversion with respect to the attention area on the basis of a luminance parallax conversion characteristic estimated by using a past frame. The parallax estimation unit is configured to perform parallax estimation on the basis of the standard image and a reference image, a viewpoint position of which is different from that of the standard image, and perform, in the attention area, the parallax estimation by using a luminance parallax conversion result obtained by the luminance parallax conversion unit.

20 Claims, 13 Drawing Sheets

US 10,430,944 B2
Page 2

Related U.S. Application Data continuation of application No. 14/221,321, filed on Mar. 21, 2014, now Pat. No. 9,213,884.

(51) Int. Cl.

| | | |
|---|---|---|
| *H04N 13/128* | (2018.01) | |
| *G01B 11/14* | (2006.01) | |
| *G06K 9/62* | (2006.01) | |
| *G01B 11/02* | (2006.01) | |
| *A61B 1/045* | (2006.01) | |
| *G06K 9/46* | (2006.01) | |
| *H04N 5/243* | (2006.01) | |
| *G06T 7/50* | (2017.01) | |
| *G06T 7/593* | (2017.01) | |
| *G06T 7/90* | (2017.01) | |
| *G06T 7/40* | (2017.01) | |
| *H04N 13/00* | (2018.01) | |
| *H04N 5/225* | (2006.01) | |

(52) U.S. Cl.
CPC ....... *G06K 9/00201* (2013.01); *G06K 9/4652* (2013.01); *G06K 9/4661* (2013.01); *G06K 9/6215* (2013.01); *G06T 7/40* (2013.01); *G06T 7/50* (2017.01); *G06T 7/593* (2017.01); *G06T 7/90* (2017.01); *H04N 5/243* (2013.01); *H04N 13/128* (2018.05); *G06K 2009/4666* (2013.01); *G06T 2207/10024* (2013.01); *G06T 2207/10068* (2013.01); *H04N 2005/2255* (2013.01); *H04N 2013/0081* (2013.01)

(56) References Cited

U.S. PATENT DOCUMENTS

| | | | |
|---|---|---|---|
| 9,213,884 B2 | 12/2015 | Uemori | |
| 9,277,202 B2* | 3/2016 | Ueno | H04N 13/111 |
| 9,737,366 B2* | 8/2017 | Miyamoto | A61B 17/3423 |
| 2005/0105610 A1* | 5/2005 | Sung | G06T 5/50 |
| | | | 375/240.01 |
| 2009/0244263 A1* | 10/2009 | Saito | G01C 3/08 |
| | | | 348/47 |
| 2010/0002073 A1* | 1/2010 | Robinson | G06T 5/002 |
| | | | 348/42 |
| 2011/0249888 A1* | 10/2011 | Caceres | G11B 15/605 |
| | | | 382/154 |
| 2012/0120202 A1* | 5/2012 | Yoon | H04N 13/239 |
| | | | 348/49 |
| 2012/0188235 A1* | 7/2012 | Wu | G06T 7/50 |
| | | | 345/419 |
| 2014/0111623 A1* | 4/2014 | Zhao | H04N 13/128 |
| | | | 348/47 |
| 2014/0132605 A1* | 5/2014 | Tsukagoshi | A61B 6/466 |
| | | | 345/424 |
| 2014/0307925 A1 | 10/2014 | Uemori | |
| 2015/0049169 A1* | 2/2015 | Krig | H04N 13/211 |
| | | | 348/46 |
| 2016/0063348 A1 | 3/2016 | Uemori | |

\* cited by examiner

IMAGE PROCESSING APPARATUS, IMAGE PROCESSING METHOD, AND PROGRAM

CROSS REFERENCE TO RELATED APPLICATIONS

This application claims the benefit under 35 U.S.C. § 120 of U.S. application Ser. No. 14/934,204 entitled "IMAGE PROCESSING APPARATUS, IMAGE PROCESSING METHOD, AND PROGRAM," filed on Nov. 6, 2015, which claims the benefit under 35 U.S.C. § 120 of U.S. application Ser. No. 14/221,321 entitled "IMAGE PROCESSING APPARATUS, IMAGE PROCESSING METHOD, AND PROGRAM" filed on Mar. 21, 2014, now U.S. Pat. No. 9,213,884, which claims priority under 35 U.S.C. § 119 to Japanese Patent Application No. JP 2013-084669 filed Apr. 15, 2013, the entire contents of which are incorporated herein by reference.

BACKGROUND

The present disclosure relates to an image processing apparatus, an image processing method, and a program, and makes it possible to estimate a parallax with high accuracy from a plurality of images with different viewpoints.

In related art, to perform displaying or the like of a 3D image, three-dimensional information of real space is obtained. For example, Japanese Patent Application Laid-open No. 2001-103513 (hereinafter, referred to as Patent Document 1) discloses a method of estimating a distance to a desired subject by using the inverse-square law, which relates to illumination, that light emitted from a light source is lowered in inverse proportion to a square of a distance. For example, in Patent Document 1, when an image of an internal organ is taken, if there is methylene blue in the image, a light absorption characteristic changes in the area. The area is detected, and a luminance component value of the image is corrected, thereby estimating a depth distance.

Further, in Japanese Patent Application Laid-open No. 2012-065851 (hereinafter, referred to as Patent Document 2), a plurality of taken images with different viewpoints are used, thereby obtaining three-dimensional information of a real space. For example, one of methods of obtaining a parallax from a taken image at a left viewpoint and a taken image at a right viewpoint is a parallax estimation that uses stereo matching based on dynamic programming (hereinafter, referred to as "DP matching parallax estimation"). In the DP matching parallax estimation, generally, a degree of matching of corresponding points (or corresponding areas) between a taken image at a left viewpoint and a taken image at a right viewpoint is obtained on a pixel or block basis, and a parallax is estimated in such a manner that the degree of matching becomes optimum (maximum) for a pixel or block line as a whole. In such a DP matching parallax estimation, the parallaxes of the pixels or blocks are determined so that the entire line becomes optimum, so even if a noise is locally generated in an image, the parallax can be stably estimated generally. Further, it is also possible to estimate an absolute distance to a subject from the parallax estimated in Patent Document 2 and a camera parameter such as a line of sight.

SUMMARY

Incidentally, in Patent Document 1, in the case where there are subjects with different light absorption characteristics in the taken image, it is difficult to accurately estimate distances to the subjects. For example, when an image of a scene of surgery is displayed as a 3D image with an endoscope system equipped with a twin-lens camera, generally, various tools (such as forceps and gauze), blood, and organs with different light absorption characteristics are mixed in the image. Therefore, it is difficult to estimate the distances by applying the inverse-square law relating to the illumination to the taken image. Further, to deal with the plurality of subjects with the different light absorption characteristics, it is necessary to find out correction coefficients of luminance components for all the subjects in advance. In addition, the estimation value obtained in Patent Document 1 is a value that indicates a degree of depth and does not indicate an absolute distance.

Further, in Patent Document 2, in the case where the degree of matching of the corresponding points (or corresponding areas) is determined, an evaluation value that indicates the degree of matching is used. For the evaluation value, for example, a sum of absolute differences (hereinafter, referred to as "SAD") of the luminance values of pixels in a block of a predetermined area or a sum of squared differences (hereinafter, referred to as "SSD") of the luminance values of the pixels in the block of the predetermined area is used. Therefore, for example, in an area where a variation in luminance value in an image is small (area with no pattern), any positions have similar evaluation values, so a correspondence error is often caused. Further, also in an area where the same pattern is repeated, areas with similar patterns have similar evaluation values, so it is difficult to obtain accurate corresponding points (or areas).

In view of the circumstances as described above, it is desirable to provide an image processing apparatus, an image processing method, and a program capable of estimating a parallax from a plurality of images with different viewpoints with high accuracy.

According to a first embodiment of the present technology, there is provided an image processing apparatus including an attention area detection unit, a luminance parallax conversion unit, and a luminance parallax conversion unit.

The attention area detection unit is configured to detect an attention area including a desired subject from a standard image.

The luminance parallax conversion unit is configured to perform a luminance parallax conversion with respect to the attention area on the basis of a luminance parallax conversion characteristic estimated by using a past frame.

The parallax estimation unit is configured to perform parallax estimation on the basis of the standard image and a reference image, a viewpoint position of which is different from that of the standard image, and perform, in the attention area, the parallax estimation by using a luminance parallax conversion result obtained by the luminance parallax conversion unit.

In the present technology, the area of the desired subject is detected as the attention area from the standard image. Further, from the parallax estimation result and the luminance value of the attention area of the past frame, the luminance parallax conversion characteristic is estimated, and the luminance parallax conversion is performed with respect to the attention area detected on the basis of the estimation result. The luminance value of the attention area is corrected in accordance with a depth distance to the desired subject, and the corrected luminance value is used to perform the luminance parallax conversion. Further, in the estimation of the luminance parallax conversion characteristic, a proportionality coefficient and an intercept are estimated on an assumption that a square root of the luminance value corrected in accordance with the depth distance is proportional to a parallax value. For example, the luminance parallax conversion characteristic is estimated on the basis of a maximum luminance value, a minimum luminance value, a maximum parallax value, and a minimum parallax value in the attention area of the past frame. Further, the maximum luminance value and the minimum luminance value may be calculated on the basis of a distribution of the luminance values and an average value of the luminance values in the attention area, and the maximum parallax value and the minimum parallax value may be calculated on the basis of a distribution of the parallax values and an average value of the parallax values in the attention area.

In addition, the similarity between the standard image and the reference image, the viewpoint position of which is different from that of the standard image, is calculated, and on the basis of the similarity calculated, the parallax estimation is performed. In the attention area detected, the luminance parallax conversion result is used to calculate the similarity. For example, a first matching area is set for each parallax estimation target position of the standard image, and a cost value that indicates a similarity between the first matching area and a second matching area corresponding to each parallax value in the reference image for each parallax value specified in advance. In the attention area detected, a cost value is calculated so as to include a cost value corresponding to a difference between the specified parallax value and the parallax value obtained by the luminance parallax conversion. In an area excluding the attention area, the cost value is calculated without the difference being obtained. Further, in the cost value, a cost value corresponding to a difference between the parallax value of the parallax estimation target position and the parallax value of a preceding parallax estimation target position in the standard image is included. The parallax value with which the cost value becomes a minimum value with the highest similarity, which is calculated in this way, is specified by dynamic programming, thereby generating the parallax estimation result. Further, the attention area is detected by comparing a color difference value and a luminance value of the standard image with predetermined threshold values or by performing a texture analysis with respect to the standard image.

According to a second embodiment of the present technology, there is provided an image processing method including detecting an attention area including a desired subject from a standard image, performing a luminance parallax conversion with respect to the attention area on the basis of a luminance parallax conversion characteristic estimated by using a past frame, and performing parallax estimation on the basis of the standard image and a reference image, a viewpoint position of which is different from that of the standard image, and performing the parallax estimation in the attention area by using a luminance parallax conversion result.

According to a third embodiment of the present technology, there is provided a program causing a computer to execute detecting an attention area including a desired subject from a standard image, performing a luminance parallax conversion with respect to the attention area on the basis of a luminance parallax conversion characteristic estimated by using a past frame, and performing parallax estimation on the basis of the standard image and a reference image, a viewpoint position of which is different from that of the standard image, and performing the parallax estimation in the attention area by using a luminance parallax conversion result.

It should be noted that the program according to the present technology is a program that can be provided to a general-purpose computer which can execute various program codes by a storage medium or a communication medium provided in a computer-readable form, for example, a storage medium such as an optical disk, a magnetic disk, and a semiconductor memory or a communication medium such as a network. Such a program is provided in a computer-readable form, thereby achieving processes in accordance with the program on the computer.

According to the present technology, for the attention area detected from the reference image, the luminance parallax conversion characteristic is determined from the luminance value of the attention area of the past frame and the parallax estimation result, and the luminance parallax conversion is performed on the basis of the estimation result. In addition, the parallax estimation based on the similarity between the standard image and the reference image the viewpoint position of which is different from that of the standard image is performed, and for the attention area, the similarity is calculated by using the luminance parallax conversion result. That is, in the attention area, not only the similarity between the standard image and the reference image but also the luminance parallax conversion result is used, thereby performing the parallax estimation. Thus, even in the case where the attention area is the image for which the parallax estimation is difficult to be performed on the basis of the similarity, it is possible to perform the parallax estimation with high accuracy from the plurality of images with different viewpoint positions.

These and other objects, features and advantages of the present disclosure will become more apparent in light of the following detailed description of best mode embodiments thereof, as illustrated in the accompanying drawings.

DETAILED DESCRIPTION OF EMBODIMENTS

Hereinafter, an embodiment of the present technology will be described. It should be noted that the description will be given in the following order.
1. Structure of image processing system
2. Structure of image processing apparatus
3. Operation of image processing apparatus
4. Other operations of image processing apparatus
<1. Structure of Image Processing System>

Figure 1A:
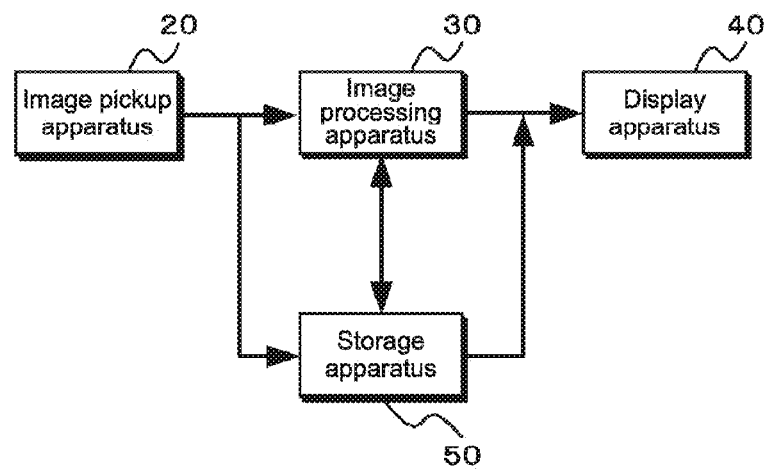
FIGS. 1A and 1B are diagrams each showing an example of the structure of an image processing system using an image processing apparatus.
Figure 1B:
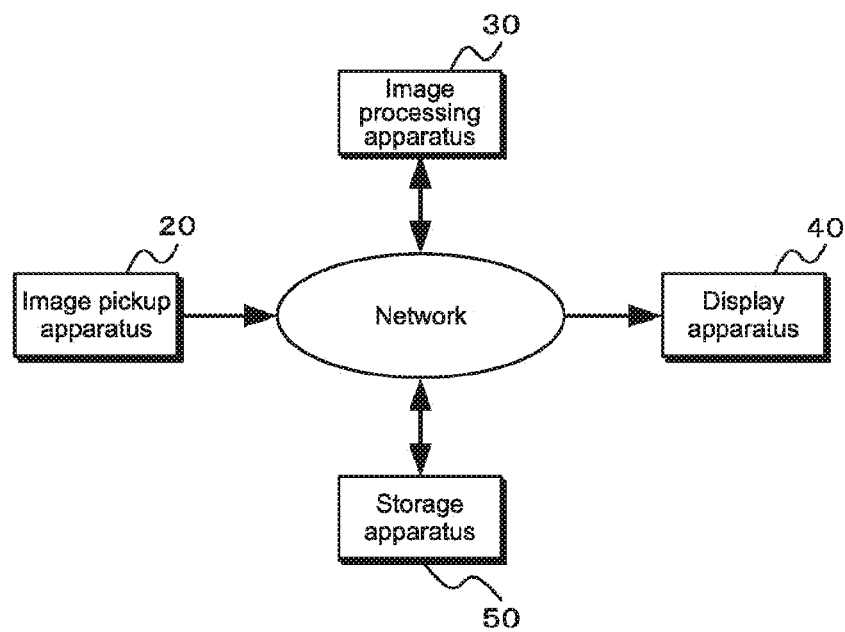

FIGS. 1A and 1B are diagrams each showing the structure of an image processing system that uses an image processing apparatus according to the present technology. An image processing system 10 includes an image pickup apparatus 20, an image processing apparatus 30, a display apparatus 40, a storage apparatus 50, and the like. As shown in FIG. 1A, the image processing apparatus 30 is connected with the image pickup apparatus 20, the display apparatus 40, and the storage apparatus 50. Further, the image processing apparatus 30 may be connected to another apparatus via a wired or wireless network as shown in FIG. 1B. Furthermore, the image processing apparatus 30 may be incorporated in any one of the image pickup apparatus 20, the display apparatus 40, and the storage apparatus 50.

The image pickup apparatus 20 generates image signals of a plurality of taken images with different viewpoint positions and supplies the signals to the image processing apparatus 30 and the storage apparatus 50. For example, the image pickup apparatus 20 generates the image signals of a taken image at a left-eye viewpoint position (hereinafter, referred to as "left image") and a taken image at a right-eye viewpoint position (hereinafter, referred to as "right eye") and supplies the image signals to the image processing apparatus 30 and the storage apparatus 50.

The image processing apparatus 30 estimates a parallax value from the image signals of the plurality of taken images with different viewpoint positions which are generated by the image pickup apparatus 20 or the image signals of the plurality of taken images with different viewpoint positions which are stored in the storage apparatus 50. The image processing apparatus 30 performs the parallax estimation by using the image signals of, for example, the left image and the right image, which are generated by the image pickup apparatus 20 or stored in the storage apparatus 50. The image processing apparatus 30 outputs a parallax estimation result to the display apparatus 40 or the storage apparatus 50. It should be noted that in the case where the parallax estimation is performed by using the image signals stored in the storage apparatus 50, the image processing apparatus 30 may output the parallax estimation result to the storage apparatus 50 and cause the storage apparatus 50 to store the result with the result and the stored image signals associated with each other.

The display apparatus 40 performs 3D image displaying. The display apparatus 40 performs the 3D image displaying on the basis of the image signals generated by the image pickup apparatus 20 or the image signals read from the storage apparatus 50 and the parallax estimation result estimated by the image processing apparatus 30.

The storage apparatus 50 stores the image signals of the plurality of taken images with different viewpoint positions which are generated by the image pickup apparatus 20 and the parallax estimation result of the image processing apparatus 30.

<2. Structure of Image Processing Apparatus>

Figure 2:
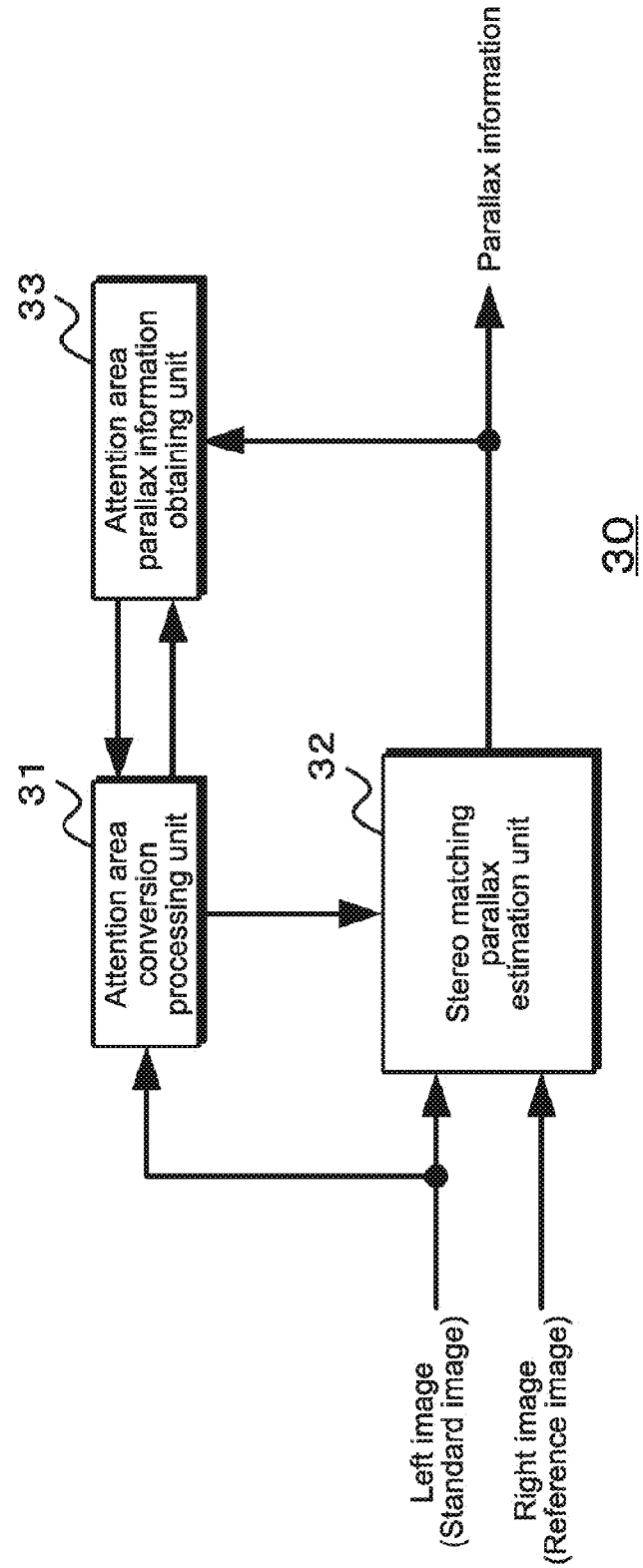
FIG. 2 is a diagram showing an example of the structure of the image processing apparatus.

FIG. 2 is a diagram showing the structure of the image processing apparatus according to the present technology. The image processing apparatus 30 includes an attention area conversion processing unit 31, a stereo matching parallax estimation unit 32, and an attention area parallax information obtaining unit 33.

The image signals of the left image and the right image which are generated by the image pickup apparatus 20 or the image signals of the left image and the right image read from the storage apparatus 50 are supplied to the stereo matching parallax estimation unit 32. Further, the image signal of the image with either one of the left image and the right image as a standard is supplied to the attention area conversion processing unit 31. For example, in the case where the left image is set as the standard, the image signal of the left image is supplied to the attention area conversion processing unit 31 with the image signal of the left image as the image signal of the standard image.

Figure 3:
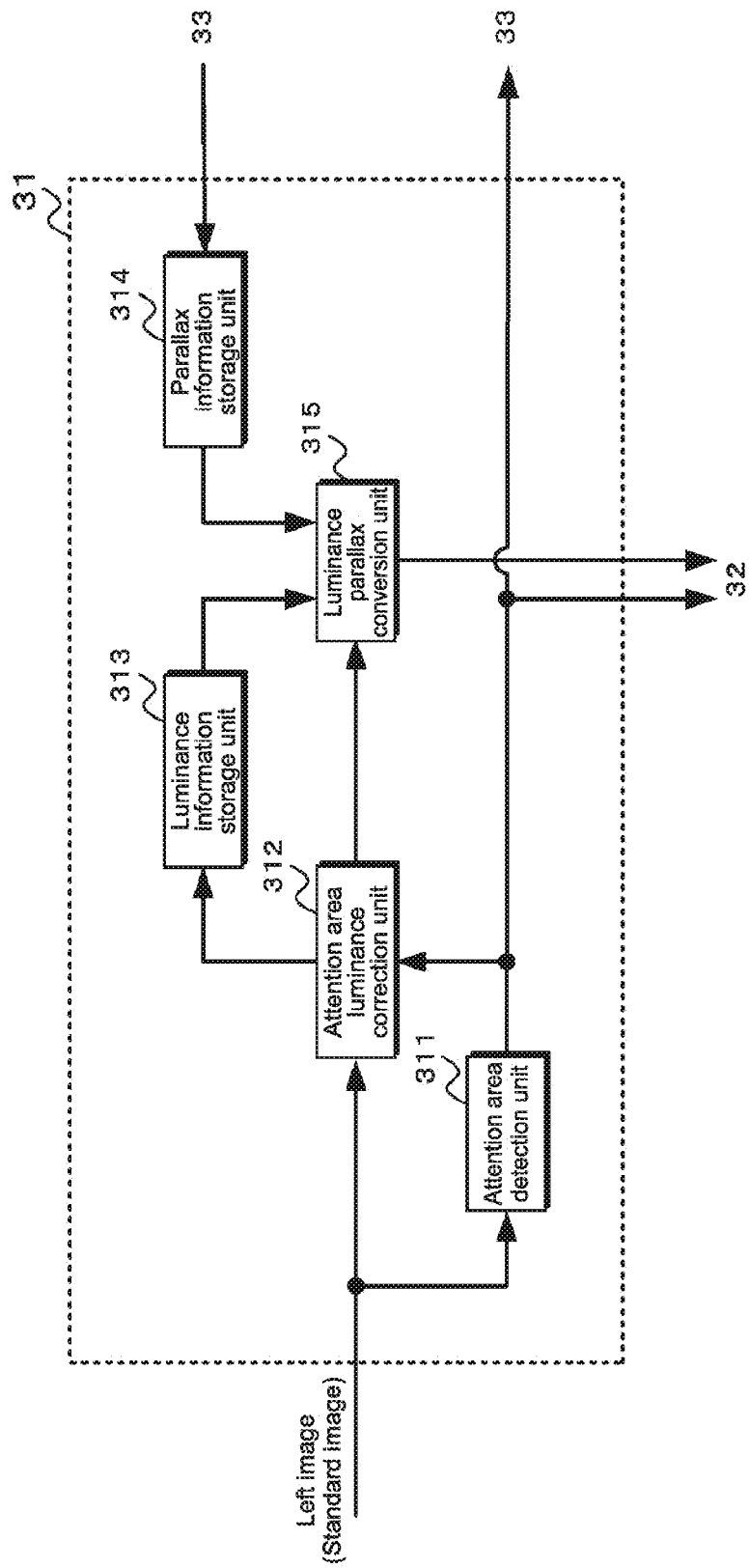
FIG. 3 is a diagram showing an example of the structure of an attention area conversion processing unit.

FIG. 3 is a diagram showing an example of the structure of the attention area conversion processing unit 31. The attention area conversion processing unit 31 includes an attention area detection unit 311, an attention area luminance correction unit 312, a luminance information storage unit 313, a parallax information storage unit 314, and a luminance parallax conversion unit 315.

The attention area detection unit 311 detects, as an attention area, an area of a desired subject (subject to be subjected to the parallax estimation) from the standard image on the basis of the image signal of the standard image. The attention area detection unit 311 outputs a detection result to the stereo matching parallax estimation unit 32 and the attention area parallax information obtaining unit 33 shown in FIG. 2 and the attention area luminance correction unit 312.

The attention area luminance correction unit 312 corrects a luminance value of a pixel in the attention area to be a luminance value corresponding to a depth distance to the desired subject. It should be noted that the depth distance will be described later with reference to FIG. 4. The attention area luminance correction unit 312 uses the corrected luminance value of the pixel in the attention area, thereby generating luminance statistics information. For example, the attention area luminance correction unit 312 calculates a function value that indicates the distribution of the luminance values, an average value, a maximum value, and a minimum value of the corrected luminance values in the attention area, for example. The attention area luminance correction unit 312 outputs the corrected luminance value to the luminance parallax conversion unit 315. In addition, the attention area luminance correction unit 312 causes the luminance information storage unit 313 to store the generated luminance statistics information therein so as to be used in the parallax estimation in a frame subsequent thereto.

The luminance information storage unit 313 stores the luminance statistics information generated by the attention area luminance correction unit 312. Further, the luminance statistics information stored in the luminance information storage unit 313 is used in the parallax estimation of the attention area in the frame subsequent thereto.

The parallax information storage unit 314 stores the parallax information of an attention area obtained by the attention area parallax information obtaining unit 33 shown in FIG. 2. Further, the parallax information stored in the parallax information storage unit 314 is used in the parallax estimation of the attention area in the frame subsequent thereto.

The luminance parallax conversion unit 315 estimates a luminance parallax conversion characteristic from a relationship between the luminance value in the attention area of the past frame and the parallax estimation result and performs a luminance parallax conversion with respect to the attention area detected by the attention area detection unit on the basis of an estimation result. Specifically, the luminance parallax conversion unit 315 makes the assumption that the square root of the luminance value corrected in accordance with the depth distance is proportional to the parallax value and estimates a proportionality coefficient and an intercept on the basis of the luminance statistics information stored in the luminance information storage unit 313 and the parallax information stored in the parallax information storage unit 314. The luminance parallax conversion unit 315 uses the proportionality coefficient and the intercept estimated, thereby performing the luminance parallax conversion and converting the corrected luminance value in the attention area to the parallax value. The luminance parallax conversion unit 315 outputs the parallax value obtained by the luminance parallax conversion to the stereo matching parallax estimation unit 32.

The stereo matching parallax estimation unit 32 shown in FIG. 2 calculates a similarity between the standard image and a reference image, the viewpoint position of which is different from that of the standard image, and performs the parallax estimation on the basis of the similarity calculated. Further, the stereo matching parallax estimation unit 32 calculates the similarity by using the luminance parallax conversion result of the luminance parallax conversion unit in the attention area detected by the attention area detection unit. The stereo matching parallax estimation unit 32 uses, for example, the image signal of the left image (standard image) and the image signal of the right image (reference image), thereby performing the stereo matching parallax estimation to calculate the parallax with respect to the left image. Further, in the case of estimating the parallax in the attention area, the stereo matching parallax estimation unit 32 uses the parallax value obtained from the luminance value of the attention area in the standard image by the attention area conversion processing unit 31, thereby performing the parallax estimation. The stereo matching parallax estimation unit 32 outputs the parallax estimation result to the attention area parallax information obtaining unit 33, the display apparatus 40, and the storage apparatus 50.

On the basis of the detection result of the attention area in the attention area detection unit 311 of the attention area conversion processing unit 31, the attention area parallax information obtaining unit 33 obtains parallax information in the attention area from the parallax information that shows the parallax estimation result by the stereo matching parallax estimation unit 32. The attention area parallax information obtaining unit 33 causes the parallax information storage unit 314 of the attention area conversion processing unit 31 to store the parallax information obtained.

<3. Operation of Image Processing Apparatus>

Next, the operation of the image processing apparatus will be described. In the attention area conversion processing unit 31, a desired subject to be subjected to the parallax estimation is limited, and the parallax is estimated from a luminance of the subject. Specifically, from the standard image, an area (attention area) of the desired subject to be subjected to the parallax estimation is detected, and the parallax value is estimated from a luminance value of the attention area. Hereinafter, a method of performing the parallax estimation by obtaining a relationship between the luminance value and the parallax value and converting the luminance value to the parallax value on the basis of the relationship between the luminance value and the parallax value is referred to as a DfL (disparity from luminance) parallax estimation method.

In the DfL parallax estimation, such a property that an intensity of reflection light from the subject is reduced in inverse proportion to the square of a distance is used. Here, a relationship between a luminance value PY obtained in the taken image and a distance r from the image pickup apparatus to a point (light source) on the subject is obtained as expressed in Expression (1).

$$PY \propto \frac{1}{r^2} \qquad (1)$$

where the symbol between the right side and the left side represents proportionality.

Figure 4:
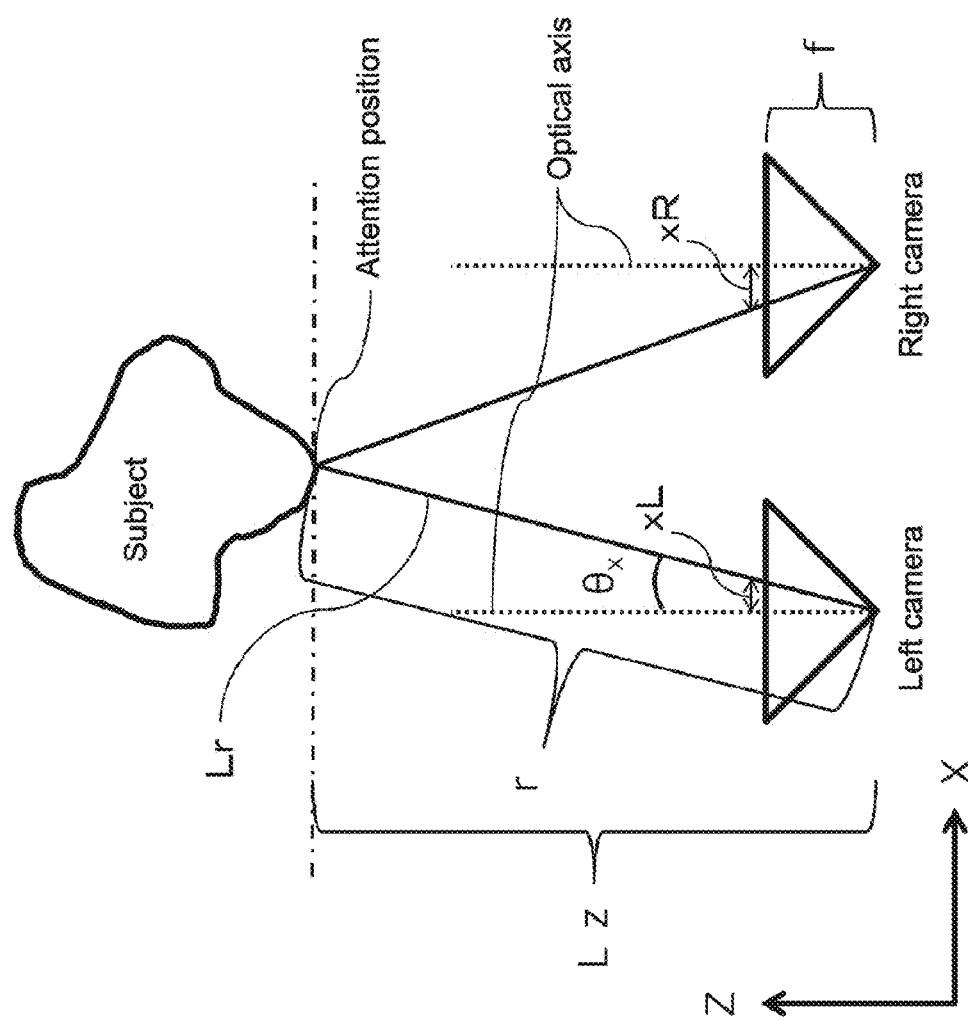
FIG. 4 is a diagram for explaining a relationship between a parallax value and a depth distance in a stereo camera.

Further, in the case where the image pickup apparatus 20 is a parallel stereo camera, and right and left optical axes are parallel as shown in FIG. 4, a relationship between a parallax value d and a depth distance Lz is obtained as expressed in Expression (2). In this case, the parallax value d refers to a value (d=xL−xR) of a difference in coordinates on right and left images, when a point (attention position of the subject) in a three-dimensional space is projected on image pickup elements of right and left cameras, and taken images are obtained. The coordinate xL is a coordinate of the attention position in an X direction with an optical axis position as a reference in the left image, and the coordinate xR is a coordinate of the attention position in the X direction with an optical axis position as a reference in the right image. It should be noted that in the case of the stereo camera shown in FIG. 4, a longitudinal (y-axis) direction corresponds to the parallax value of "0", and a lateral (x-axis) direction corresponds to the parallax value d.

$$d \propto \frac{1}{Lz} \qquad (2)$$

As shown in FIG. 4, the distance r is an optical path distance from the image pickup apparatus to the point (light source) on the subject, and the depth distance Lz is parallel to the optical axes of the image pickup apparatus and is a distance from the image pickup apparatus to the point (light source) on the subject. A relationship between the distance (optical path distance) r and the depth distance Lz is determined as expressed in Expression (3). It should be noted that ex is an angle formed by the optical axis and a direction to the attention position on an XZ plane.

$$Lz = r \cos \theta_x \qquad (3)$$

Further, FIG. 4 is a diagram showing the XZ plane (diagram showing the relationship between the image pickup apparatus and the subject viewed from above), but when an actual three-dimensional space, that is, a positional relationship in a vertical direction between the image pickup apparatus and the subject is included, the relationship between the optical path distance r and the depth distance Lz is determined as expressed in Expression (4). It should be noted that θy is an angle formed by the optical axis and the direction to the attention position on a YZ plane.

$$Lz = r \cos \theta_x \cos \theta_y \qquad (4)$$

Thus, on the basis of Expressions (1), (2), and (4), the relationship between the parallax value and the luminance value is determined as expressed in Expression (5), and the parallax value d has a proportional relationship with the square root of a corrected luminance value PYC. In Expression (5), the corrected luminance value PYC is calculated by a correction expression as expressed in Expression (6).

It should be noted that in Expressions (3), (4), and (6), a cosine value of the angle θx formed by the optical axis of the image pickup apparatus and the attention position direction can be calculated from a focal length of the image pickup apparatus and the coordinate of the point (light source) on the subject in the taken image. For example, as shown in FIG. 4, when the coordinate of the point (light source) in the X-axis direction on the subject is "xL", and the focal distance of the image pickup apparatus is represented by "f" with the optical axis position in the left image as a reference, it is possible to calculate a cosine value of the angle θx on the basis of Expression (7). Further, for the YZ plane, when the coordinate of the point (light source) in the Y-axis direction on the subject is "yL" with the optical axis position in the left image as a reference, it is possible to calculate a cosine value of the angle θy on the basis of Expression (8).

$$d \propto \sqrt{PYC} \quad (5)$$

$$PYC = \frac{PY}{(\cos\theta_x \cos\theta_y)^2} \quad (6)$$

$$\cos\theta_x = \frac{f}{\sqrt{xL^2 + f^2}} \quad (7)$$

$$\cos\theta_y = \frac{f}{\sqrt{yL^2 + f^2}} \quad (8)$$

As shown in Expression (5), the parallax value d has a proportional relationship with the square root of the corrected luminance value PYC. Therefore, by obtaining a proportionality coefficient and an intercept, it is possible to convert the corrected luminance value PYC into the parallax value d.

The luminance parallax conversion characteristic in the case of converting the luminance value into the parallax value is estimated from the luminance value of the attention area of the past frame and the parallax estimation result. As a result, it is possible to perform the luminance parallax conversion without previously checking the information relating to the light absorption characteristic of the subject and the light source. In addition, the luminance parallax conversion characteristic is estimated by using the luminance value of the past frame for each attention area and the parallax estimation result, with the result that it is possible to perform the parallax estimation for each of the subjects even if the plurality of subjects with different light absorption characteristics are mixed.

Next, the operation in the attention area conversion processing unit 31 will be described. In the attention area conversion processing unit 31, the luminance value is converted into the parallax value as described above, so a color space format of the standard image is set as "Y (luminance), Cr (red color difference), and Cb (blue color difference)", and an image signal of the color space format is used to perform the attention area parallax estimation. Therefore, in the case where the image signal supplied from the image pickup apparatus 20 or the like is an image signal of another format, for example, three primary color signal, the attention area conversion processing unit 31 performs a format conversion and then performs the parallax estimation.

Further, in the case where the image signal output from the image pickup apparatus 20 is an image signal for which a luminance correction has been performed, the relationship between the luminance value PY and the distance r does not satisfy the relationship expressed by Expression (1). Therefore, the attention area conversion processing unit 31 performs an inverse correction corresponding to the luminance correction by the image pickup apparatus 20. For example, in the case where a gamma correction is performed in the image pickup apparatus 20, an inverse gamma correction that the image signal output from the image pickup apparatus 20 is returned to the image signal before the gamma correction is performed, then the parallax estimation is performed. It should be noted that, in the case where the image signal output from the image pickup apparatus 20 is stored in the storage apparatus 50, and the image signal stored in the storage apparatus 50 is used to perform the parallax estimation, the inverse correction and the format conversion described above may be performed by the storage apparatus 50.

The attention area detection unit 311 of the attention area conversion processing unit 31 detects the attention area on the basis of the image signal of the standard image. The attention area detection unit 311 uses a preset threshold value in accordance with the luminance and color of the desired subject, thereby performing segmentation of the attention area, for example. Specifically, the attention area detection unit 311 has threshold values TH_min_Y and TH_max_Y with respect to the luminance value PY, threshold values TH_min_Cr and TH_max_Cr with respect to a red color difference value PCr, and threshold values TH_min_Cb and TH_max_Cb with respect to a blue color difference value PCb. The attention area detection unit 311 detects, as the attention area, such an area that the luminance value PY falls within the range of the threshold values TH_min_Y to TH_max_Y, the red color difference value PCr falls within the range of the threshold values TH_min_Cr to TH_max_Cr, and the blue color difference value PCb falls within the range of the threshold values TH_min_Cb to TH_max_Cb.

The threshold values TH_min_Y, TH_max_Y, TH_min_Cr, TH_max_Cr, TH_min_Cb, and TH_max_Cb are set by finding out in advance components of the color difference and the luminance of the desired subject from the taken image of the desired subject. For example, in the case of an image obtained by an endoscope, color difference components of an inner wall surface inside a body and a specific organ are found out in advance, and threshold values are set with respect to the color difference values so that only those areas can be extracted. In this way, by setting the threshold values appropriately, it is possible to exclude the other subjects with different light absorption characteristics. Further, for the luminance value, by excluding such high luminance pixels that flared highlights are generated and such low luminance pixels that blocked up shadows are generated, a subject whose parallax is difficult to be estimated on the basis of the luminance value due to the flared highlights and the blocked up shadows is excluded from parallax estimation targets.

The attention area luminance correction unit 312 of the attention area conversion processing unit 31 performs the correction of the luminance value with respect to the pixel in the attention area detected by the attention area detection unit 311. The attention area luminance correction unit 312 performs calculation of Expressions (7) and (8) on the basis of the pixel position and the focal distance for each pixel in the attention area in the standard image, thereby determining a cosine value of an angle formed by the optical axis of the image pickup apparatus 20 and a straight line Lr in a direction to an attention position in the attention area. Further, the attention area luminance correction unit 312 performs calculation of Expression (6) by using the cosine value calculated, thereby correcting the luminance value of each pixel in the attention area.

In addition, the attention area luminance correction unit 312 uses the corrected luminance value PYC of the pixels in the attention area, thereby generating the luminance statistic information. The attention area luminance correction unit 312 determines a maximum luminance value PYCmax and a minimum luminance value PYCmin of the luminance values after the correction in the attention area. Further, the attention area luminance correction unit 312 may calculate an average luminance value PYCavg and a function value that indicates a distribution of the luminance values after the correction in the attention area, such as a standard deviation.

Figure 5:
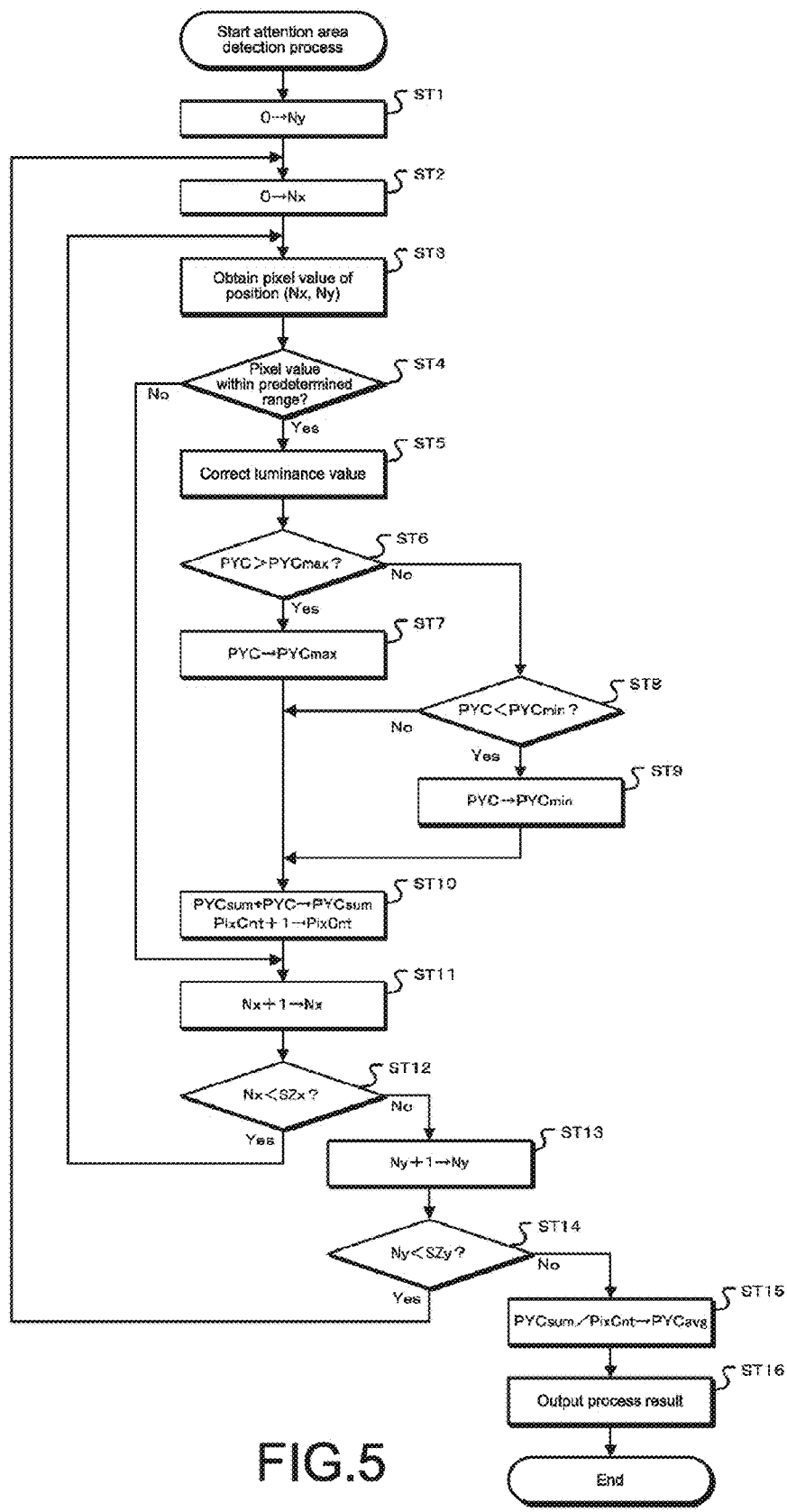
FIG. 5 is a flowchart showing an example of operations of an attention area detection unit and an attention area luminance correction unit.

FIG. 5 is a flowchart showing an example of the operation of the attention area detection unit and the attention area luminance correction unit. In Step ST1, the attention area detection unit 311 initializes a coordinate value Ny that indicates the position in the Y direction to set the coordinate value Ny to "0" and then proceeds to Step ST2.

In Step ST2, the attention area detection unit 311 initializes a coordinate value Nx that indicates the position in the X direction to set the coordinate value Nx to "0" and then proceeds to Step ST3.

In Step ST3, the attention area detection unit 311 obtains a pixel value of the position (Nx, Ny). The attention area detection unit 311 obtains the luminance value and the color difference value of the position (Nx, Ny) and then proceeds to Step ST4.

In Step ST4, the attention area detection unit 311 determines whether the pixel value falls within a predetermined range or not. The attention area detection unit 311 compares the luminance value and the color difference value with preset threshold values, and when the color difference value and the luminance value is the color of the attention area and a luminance within the predetermined range, respectively, the attention area detection unit 311 proceeds to Step ST5. When the color difference value is not the color of the attention area, and the luminance value is not within the predetermined range, the attention area detection unit 311 proceeds to Step ST12.

In Step ST5, the attention area luminance correction unit 312 performs the correction of the luminance value. The attention area luminance correction unit 312 calculates Expression (6) mentioned above to correct the luminance value, outputs the corrected luminance value PYC to the luminance parallax conversion unit 315, and proceeds to Step ST6.

In Step ST6, the attention area luminance correction unit 312 determines whether the corrected luminance value PYC is larger than the maximum luminance value PYCmax or not. When the corrected luminance value PYC is larger than the maximum luminance value PYCmax, the attention area luminance correction unit 312 proceeds to Step ST7. When the corrected luminance value PYC is equal to or smaller than the maximum luminance value PYCmax, the attention area luminance correction unit 312 proceeds to Step ST8. It should be noted that in the case where the pixel on the position (Nx, Ny) is the first pixel which is determined to be the attention area, the corrected luminance value PYC of the pixel on the position (Nx, Ny) is set as an initial value of the minimum luminance value PYCmin to be described later and the maximum luminance value PYCmax.

In Step ST7, the attention area luminance correction unit 312 sets the corrected luminance value PYC to the maximum luminance value PYCmax and proceeds to Step ST10.

In Step ST8, the attention area luminance correction unit 312 determines whether the corrected luminance value PYC is smaller than the minimum luminance value PYCmin or not. When the corrected luminance value PYC is smaller than the minimum luminance value PYCmin, the attention area correction unit 312 proceeds to Step ST9. When the corrected luminance value PYC is equal to or larger than the minimum luminance value PYCmin, the attention area correction unit 312 proceeds to Step ST10.

In Step ST9, the attention area luminance correction unit 312 sets the corrected luminance value PYC to the minimum luminance value PYCmin and then proceeds to Step S10.

In Step ST10, the attention area luminance correction unit 312 updates a luminance integration value and a pixel count integration value. The attention area luminance correction unit 312 adds the corrected luminance value PYC to a luminance integration value PYCsum and sets an addition result as a new luminance integration value PYCsum. Further, the attention area luminance correction unit 312 adds "1" to a pixel count integration value PixCnt, sets an addition result as a new pixel count integration value PixCnt, and proceeds to Step ST11. It should be noted that initial values of the luminance integration value PYCsum and the pixel count integration value PixCnt are set to "0".

In Step ST11, the attention area detection unit 311 updates the coordinate position in the X direction. The attention area detection unit 311 adds "1" to the coordinate value Nx, sets an addition result as a new coordinate value Nx, and proceeds to Step ST12.

In Step ST12, the attention area detection unit 311 determines whether the coordinate position in the X direction exceeds the range of the standard image or not. In the case where the standard image has a pixel count SZx in the X direction, the attention area detection unit 311 determines whether the coordinate value Nx is smaller than the pixel count SZx or not. Here, in the case where the coordinate value Nx falls within the range of "0 to (SZx−1)", the position indicated by the coordinate value Nx is a position in the standard image, and in the case where the coordinate value Nx is "SZx", the position indicated by the coordinate value Nx is a position outside the range of the standard image. Therefore, when it is determined that the coordinate value Nx is smaller than the pixel count SZx, the attention area detection unit 311 returns to Step ST3 with the determination of being within the range of the standard image. Further, in the case where the coordinate value Nx is equal to or larger than the pixel count SZx, the attention area detection unit 311 determines that the process for one line in the standard image is terminated and proceeds to Step ST13.

In Step ST13, the attention area detection unit 311 updates a coordinate position in the Y direction. The attention area detection unit 311 adds "1" to the coordinate value Ny that indicates the coordinate position in the Y direction, sets an addition result as a new coordinate value Ny, and then proceeds to Step ST14.

In Step ST14, the attention area detection unit 311 determines whether the coordinate position in the Y direction exceeds the range of the standard image or not. In the case where the standard image has a pixel count SZy in the Y direction, the attention area detection unit 311 determines whether the coordinate value Ny is smaller than the pixel count SZy or not. Here, in the case where the coordinate value Ny falls within the range of "0 to (SZy−1)", the position indicated by the coordinate value Ny is a position in the standard image, and in the case where the coordinate value Ny is "SZy", the position indicated by the coordinate value Ny is a position outside the range of the standard image. Therefore, when it is determined that the coordinate value Ny is smaller than the pixel count SZy, the attention area detection unit 311 returns to Step ST2 with the determination of being within the range of the standard image. Further, in the case where the coordinate value Ny is equal to or larger than the pixel count SZy, the attention area detection unit 311 determines that the process for one line in the standard image is terminated and proceeds to Step ST15.

In Step ST15, the attention area luminance correction unit 312 calculates an average luminance value. The detection process for the attention area with respect to the one frame of the standard image is terminated, and then the attention area luminance correction unit 312 divides the luminance integration value PYCsum of the pixels in the attention area by the pixel count integration value PixCnt that indicates the pixel count in the attention area, thereby obtaining the average luminance value PYCavg. The attention area luminance correction unit 312 proceeds to Step ST16 after the calculation of the average luminance value. It should be noted that the attention area luminance correction unit 312 may calculate a luminance statistics amount that indicates a distribution of the luminance values in the attention area, such as a standard deviation and dispersion.

In Step ST16, the attention area detection unit 311 and the attention area distribution correction unit 312 output results of the processes. On the basis of the determination result in Step ST4, the attention area detection unit 311 outputs attention area information that indicates the attention area in the standard image to the stereo matching parallax estimation unit 32 and the attention area parallax information obtaining unit 33. Further, the attention area distribution correction unit 312 outputs the maximum luminance value PYCmax, the minimum luminance value PYCmin, the average luminance value PYCavg, and the like to the luminance information storage unit 313 as the luminance statistic information and then terminates the process for one frame of the standard image.

In the luminance information storage unit 313, the luminance statistics information generated in the attention area distribution correction unit 312 is stored. In the parallax information storage unit 314, the parallax information of the attention area obtained in the attention area parallax information obtaining unit 33 are stored. The luminance parallax conversion unit 315 calculates a proportionality coefficient and an intercept from the luminance statistics information stored in the luminance information storage unit 313 and the parallax information stored in the parallax information storage unit 314. Further, the luminance parallax conversion unit 315 uses the calculated proportionality coefficient and intercept to perform the luminance parallax conversion, thereby converting the corrected luminance value in the attention area to the parallax value.

Here, a description will be given on the attention area parallax information obtaining unit 33, prior to a description on an operation of the luminance parallax conversion unit 315. To the attention area parallax information obtaining unit 33, the parallax information is supplied from the stereo matching parallax estimation unit 32. Further, to the attention area parallax information obtaining unit 33, the attention area information is supplied from the attention area detection unit 311. On the basis of the attention area information, the attention area parallax information obtaining unit 33 performs an information extraction process with respect to the parallax information supplied from the stereo matching parallax estimation unit 32, thereby extracting the parallax information of the attention area. Further, on the basis of the extracted parallax information of the attention information, the attention area parallax information obtaining unit 33 calculates a parallax statistics amount such as a maximum parallax value, a minimum parallax value, an average parallax value, and a function value that indicates a distribution of the parallax values and outputs the values to the parallax information storage unit 314.

Figure 6:
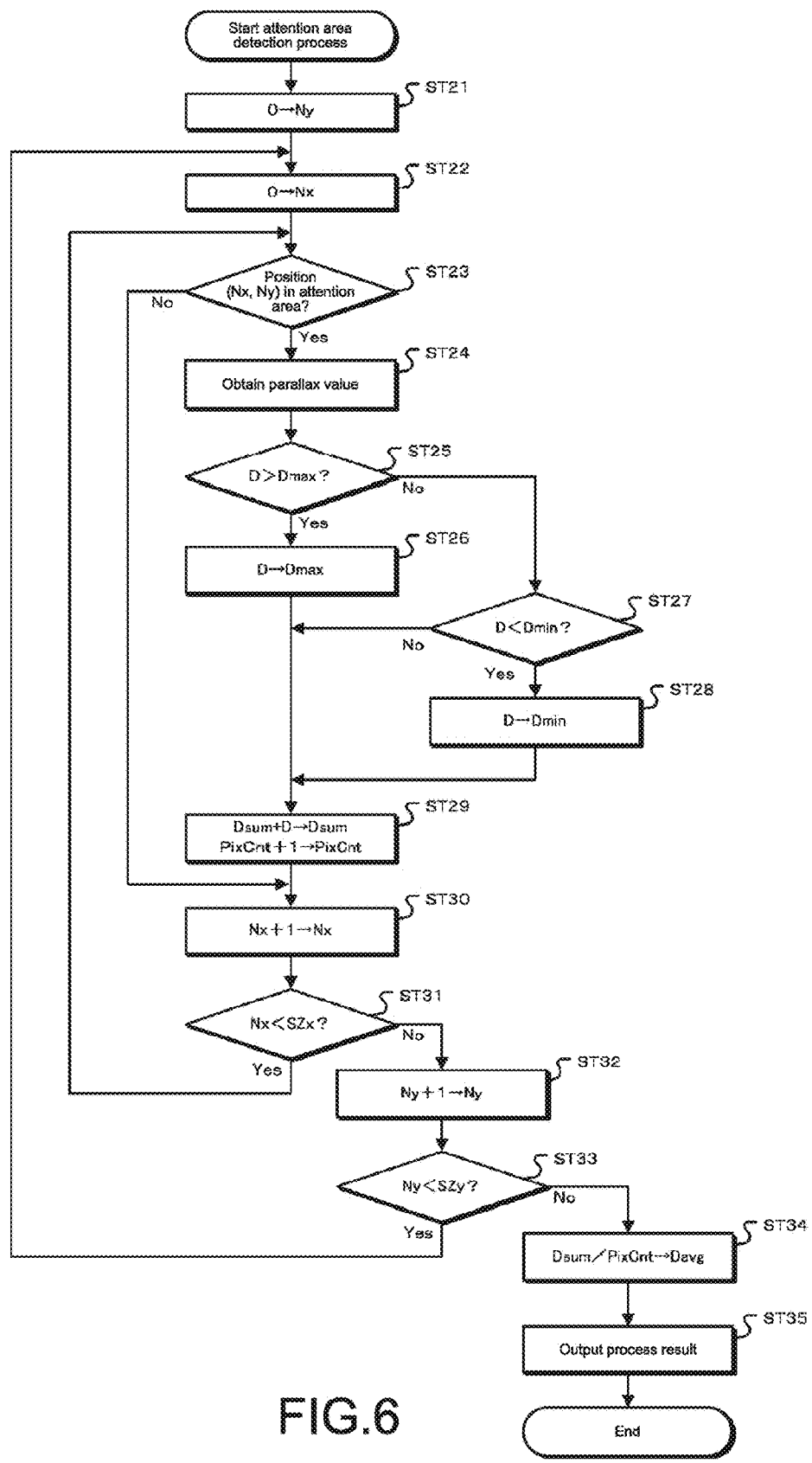
FIG. 6 is a flowchart showing an example of an operation a parallax information obtaining unit.

FIG. 6 is a flowchart showing an example of an operation of the parallax information obtaining unit. In Step ST21, the attention area parallax information obtaining unit 33 initializes the coordinate value Ny that indicates the coordinate position in the Y direction, sets the coordinate value Ny to "0", and proceeds to Step ST22.

In Step ST22, the attention area parallax information obtaining unit 33 initializes the coordinate value Nx that indicates the position in the X direction, sets the coordinate value Nx to "0", and then proceeds to Step ST23.

In Step ST23, the attention area parallax information obtaining unit 33 determines whether the position (Nx, Ny) is in the attention area or not. On the basis of the attention area information, when it is determined that the position (Nx, Ny) is in the attention area, the attention area parallax information obtaining unit 33 proceeds to Step ST24, and when it is determined that the position is outside of the attention area, the attention area parallax information obtaining unit 33 proceeds to Step ST30.

In Step ST24, the attention area parallax information obtaining unit 33 extracts the parallax value. The attention area parallax information obtaining unit 33 extracts the parallax value of the position (Nx, Ny) and proceeds to Step ST25.

In Step ST25, the attention area parallax information obtaining unit 33 determines whether a parallax value D of the position (Nx, Ny) is larger than a maximum parallax value Dmax or not. When the parallax value D is larger than the maximum parallax value Dmax, the attention area parallax information obtaining unit 33 proceeds to Step ST26. When the parallax value D is equal to or smaller than the maximum parallax value Dmax, the attention area parallax information obtaining unit 33 proceeds to Step ST27. It should be noted that in the case where the position (Nx, Ny) is the first pixel determined as the attention area, the parallax value D of the position (Nx, Ny) is set as an initial value of the minimum parallax value Dmin to be described later and the maximum parallax value Dmax.

In Step ST26, the attention area parallax information obtaining unit 33 sets the parallax value D of the position (Nx, Ny) to the maximum parallax value Dmax and proceeds to Step ST29.

In Step ST27, the attention area parallax information obtaining unit 33 determines whether the parallax value D of the position (Nx, Ny) is smaller than the minimum parallax value Dmin or not. When the parallax value D is smaller than the minimum parallax value Dmin, the attention area parallax information obtaining unit 33 proceeds to Step ST28. When the parallax value D is equal to or larger than the minimum parallax value Dmin, the attention area parallax information obtaining unit 33 proceeds to Step ST29.

In Step ST28, the attention area parallax information obtaining unit 33 sets the parallax value D of the position (Nx, Ny) to the minimum parallax value Dmin and proceeds to Step ST29.

In Step ST29, the attention area parallax information obtaining unit 33 updates the parallax integration value and the pixel count integration value. The attention area parallax information obtaining unit 33 adds the parallax value D of the position (Nx, Ny) to a parallax integration value Dsum, and sets an addition result as a new parallax integration value Dsum. Further, the attention area parallax information obtaining unit 33 adds "1" to a pixel count integration value PixCnt, sets an addition result as a new pixel count integration value PixCnt, and proceeds to Step ST30. It should be noted that the initial values of the parallax integration value Dsum and the pixel count integration value PinCnt are set to "0".

In Step ST30, the attention area parallax information obtaining unit 33 updates the coordinate position in the X direction. The attention area detection unit 311 adds "1" to the coordinate value Nx, sets an addition result as a new coordinate value Nx, and proceeds to Step ST31.

In Step ST31, the attention area parallax information obtaining unit 33 determines whether the coordinate position in the X direction exceeds the range of the standard image or not. In the case where the standard image has the pixel count SZx in the X direction, the attention area parallax information obtaining unit 33 determines whether the coordinate value Nx is smaller than the pixel count SZx or not. Here, in the case where the coordinate value Nx falls within the range of "0 to (SZx−1)", the position indicated by the coordinate value Nx is a position in the standard image, and in the case where the coordinate value Nx is "SZx", the position indicated by the coordinate value Nx is a position outside the range of the standard image. Therefore, when it is determined that the coordinate value Nx is smaller than the pixel count SZx, the attention area parallax information obtaining unit 33 returns to Step ST23 with the determination of being within the range of the standard image. Further, in the case where the coordinate value Nx is equal to or larger than the pixel count SZx, the attention area parallax information obtaining unit 33 determines that the process for one line in the standard image is terminated and proceeds to Step ST32.

In Step ST32, the attention area parallax information obtaining unit 33 updates the coordinate position in the Y direction. The attention area parallax information obtaining unit 33 adds "1" to the coordinate value Ny that indicates the coordinate position in the Y direction, sets an addition result as a new coordinate value Ny, and then proceeds to Step ST33.

In Step ST33, the attention area parallax information obtaining unit 33 determines whether the coordinate position in the Y direction exceeds the range of the standard image or not. In the case where the standard image has a pixel count SZy in the Y direction, the attention area parallax information obtaining unit 33 determines whether the coordinate value Ny is smaller than the pixel count SZy or not. Here, in the case where the coordinate value Ny falls within the range of "0 to (SZy−1)", the position indicated by the coordinate value Ny is a position in the standard image, and in the case where the coordinate value Ny is "SZy", the position indicated by the coordinate value Ny is a position outside the range of the standard image. Therefore, when it is determined that the coordinate value Ny is smaller than the pixel count SZy, the attention area parallax information obtaining unit 33 returns to Step ST22 with the determination of being within the range of the standard image. Further, in the case where the coordinate value Ny is equal to or larger than the pixel count SZy, the attention area parallax information obtaining unit 33 determines that the process for one line in the standard image is terminated and proceeds to Step ST34.

In Step ST34, the attention area parallax information obtaining unit 33 calculates an average luminance value. The obtaining process with respect to the one frame of the standard image is terminated, and then the attention area parallax information obtaining unit 33 divides the parallax integration value Dsum of the pixels in the attention area by the pixel count integration value PixCnt that indicates the pixel count in the attention area, thereby obtaining an average parallax value Davg. The attention area parallax information obtaining unit 33 proceeds to Step ST35 after the calculation of the average parallax value. It should be noted that the attention area parallax information obtaining unit 33 may calculate a parallax statistics amount that indicates a distribution of the parallax values in the attention area, such as a standard deviation and dispersion.

In Step ST35, the attention area parallax information obtaining unit 33 outputs results of the processes. The attention area parallax information obtaining unit 33 outputs the average parallax value Davg to the parallax information storage unit 314 along with the maximum parallax value Dmax and the minimum parallax value Dmin, as the parallax statistics information, and then terminates the process for one frame of the standard image.

The luminance parallax conversion unit 315 estimates a luminance parallax conversion characteristic from the luminance information of the past frame stored in the luminance information storage unit 313 and the parallax information of the past frame stored in the parallax information storage unit 314. Specifically, as expressed in Expression (5) mentioned above, the luminance parallax conversion unit 315 makes the assumption that the square root of the corrected luminance value corresponding to the depth distance is proportional to the parallax value and calculates a proportionality coefficient $K^{DfL}$ and an intercept C in Expression (9). It should be noted that the parallax value calculated on the basis of Expression (9) is set as a DfL parallax value $d^{DfL}$.

$$d^{DfL} = K^{DfL}\sqrt{PYC} + C \qquad (9)$$

In the case where the parallax estimation is performed by using a moving image obtained by shooting the desired subject, the parallax value in the attention area has a small difference from the parallax value of the attention area in a preceding frame. Further, by using the maximum parallax value, the minimum parallax value, the maximum luminance value, and the minimum luminance value after the correction in the attention area, the luminance value range and the parallax value range in the attention area are maximized, with the result that it is possible to estimate the relationship between the luminance value and the parallax value of the pixels in the attention area with high accuracy. Therefore, the luminance parallax conversion unit 315 uses the maximum parallax value Dmax and minimum parallax value Dmin and the maximum luminance value PYCmax and minimum luminance value PYCmin after the correction in the attention area of the past frame, for example, the preceding frame, thereby calculating the proportionality coefficient $K^{DfL}$ and the intercept C.

Figure 7:
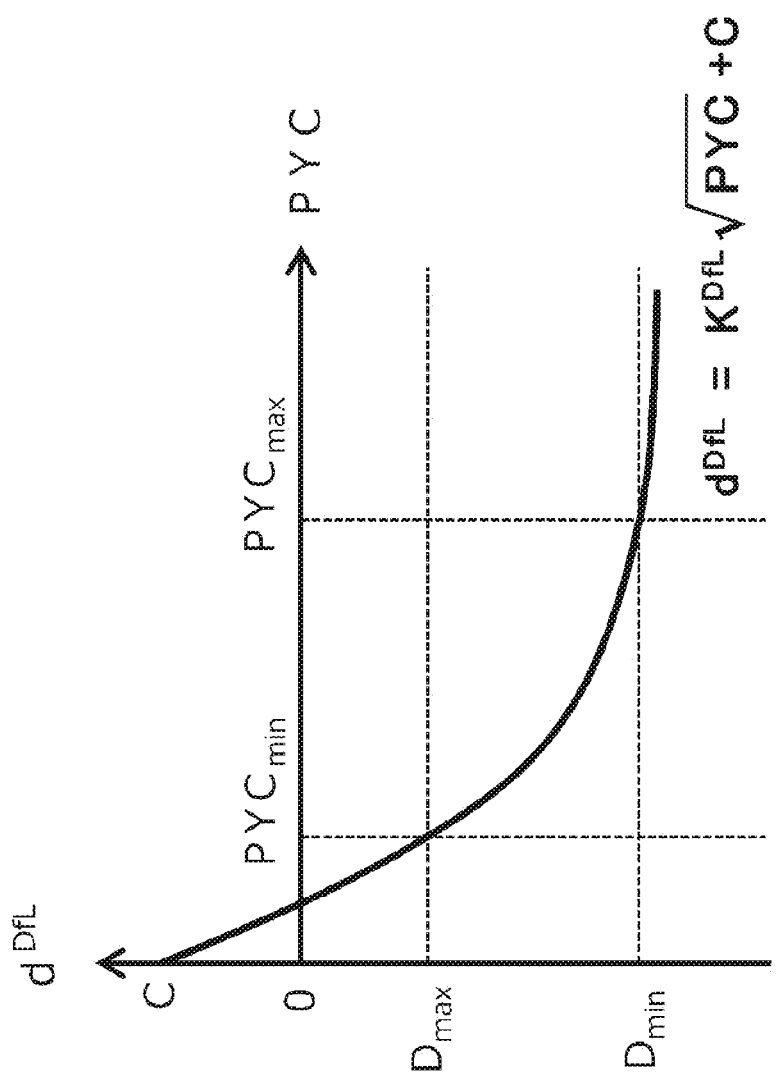
FIG. 7 is a diagram showing an relationship between a luminance value and a parallax value in the case where a left image is set as a standard image.

In the case where the left image is set as the standard image, the parallax value of the attention area is a negative value at all times. Therefore, a characteristic curve of the function expressed by Expression (9) is a curve that passes two points of (PYCmin, Dmax) and (PYCmax, Dmin) as shown in FIG. 7. Therefore, the proportionality coefficient $K^{DfL}$ can be calculated on the basis of Expression (10), and the intercept C can be calculated on the basis of Expression (11).

$$K^{DfL} = \frac{D_{min} - D_{max}}{\sqrt{PYC_{max}} - \sqrt{PYC_{min}}} \quad (10)$$

$$C = \frac{D_{max}\sqrt{PYC_{max}} - D_{min}\sqrt{PYC_{min}}}{\sqrt{PYC_{max}} - \sqrt{PYC_{min}}} \quad (11)$$

It should be noted that in the case of setting the left image as the standard image, because the parallax value of the attention area is the negative value at all times, in the case where a calculation result of Expression (9) by using the proportionality coefficient $K^{DfL}$ and the intercept C is a positive value, the DfL parallax value $d^{DfL}$ is set to "0".

Figure 8:
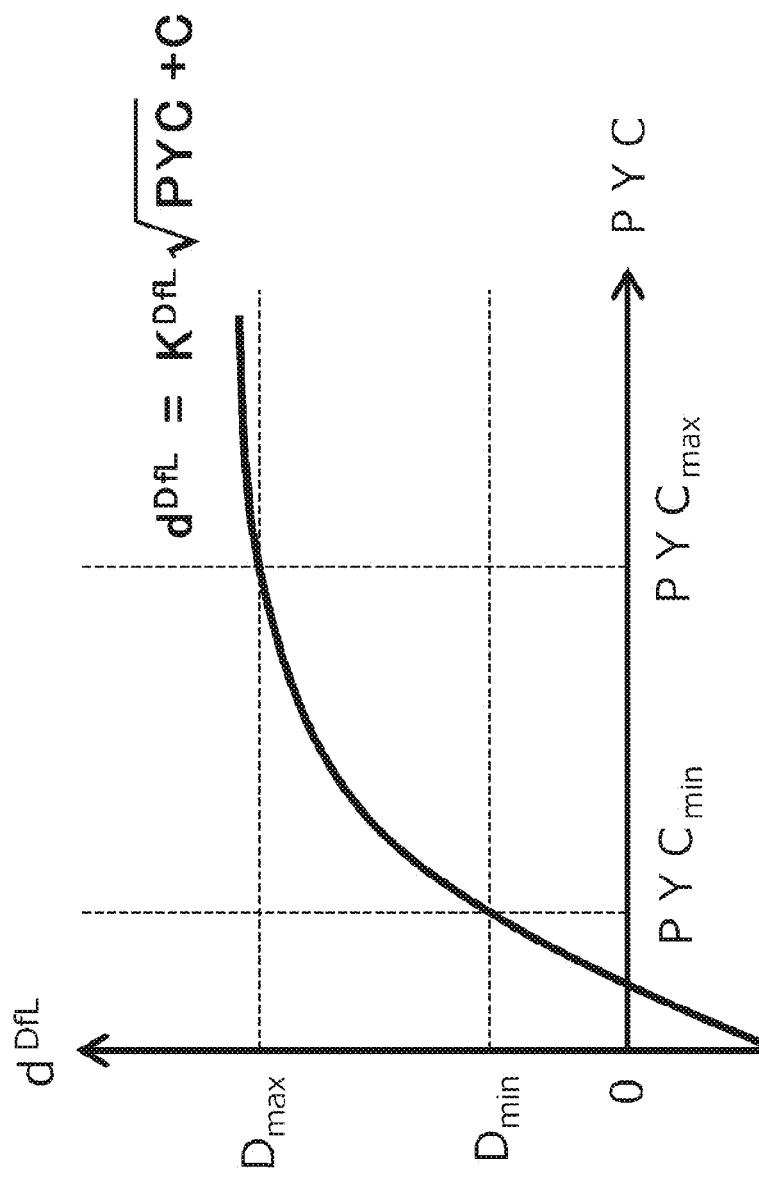
FIG. 8 is a diagram showing an relationship between a luminance value and a parallax value in the case where a right image is set as a standard image.

In the case of setting the right image as the standard image, the parallax value of the attention area is a positive value at all times. Therefore, the characteristic curve of the function expressed by Expression (9) is a curve that passes two points of (PYCmin, Dmin) and (PYCmax, Dmax) as shown in FIG. 8. Therefore, the proportionality coefficient $K^{DfL}$ can be determined on the basis of Expression (12), and the intercept C can be determined on the basis of Expression (13).

$$K^{DfL} = \frac{D_{max} - D_{min}}{\sqrt{PYC_{max}} - \sqrt{PYC_{min}}} \quad (12)$$

$$C = \frac{D_{min}\sqrt{PYC_{max}} - D_{max}\sqrt{PYC_{min}}}{\sqrt{PYC_{max}} - \sqrt{PYC_{min}}} \quad (13)$$

It should be noted that in the case of setting the right image as the standard image, because the parallax value of the attention area is the positive value at all times, in the case where a calculation result of Expression (9) by using the proportionality coefficient $K^{DfL}$ and the intercept C is a negative value, the DfL parallax value $d^{DfL}$ is set to "0".

The luminance parallax conversion unit 315 performs estimation of the luminance parallax conversion characteristic as described above and performs the luminance parallax conversion with the luminance parallax conversion characteristic estimated.

Figure 9:
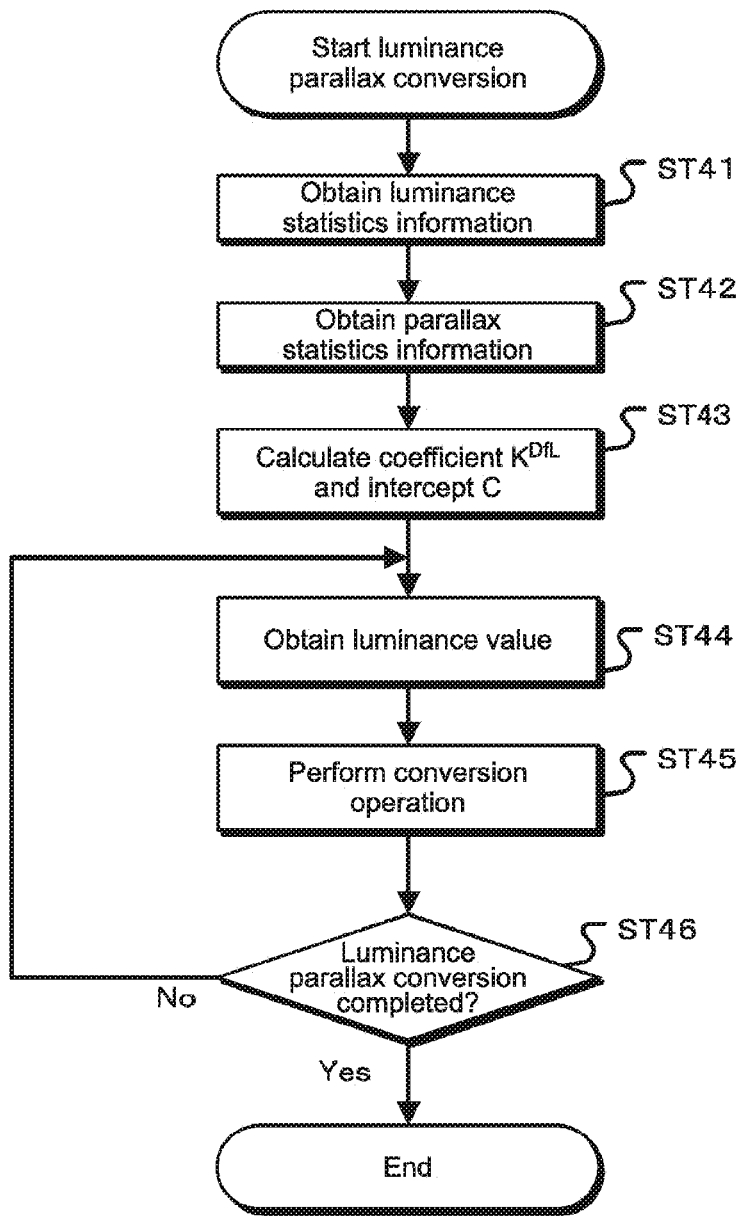
FIG. 9 is a flowchart showing an example of an operation of a luminance parallax conversion unit.

FIG. 9 is a flowchart showing an example of an operation of the luminance parallax conversion unit. In Step ST41, the luminance parallax conversion unit 315 obtains luminance statistics information. The luminance parallax conversion unit 315 obtains the luminance statistics information stored in the luminance information storage unit 313, for example, a maximum luminance value and a minimum luminance value of the corrected luminance values of the attention area in the standard image of a preceding frame, and then proceeds to Step ST42.

In Step ST42, the luminance parallax conversion unit 315 obtains parallax statistics information. The luminance parallax conversion unit 315 obtains the parallax statistics information stored in the parallax information storage unit 314, for example, a maximum parallax value and a parallax value in the parallax estimation result of the attention area in the standard image of a preceding frame, and then proceeds to Step ST43.

In Step ST43, the luminance parallax conversion unit 315 determines the proportionality coefficient and the intercept. In the case of setting the left image as the standard image, the luminance parallax conversion unit 315 uses the luminance statistics information and the parallax statistics information to calculate Expressions (10) and (11), determines the proportionality coefficient $K^{DfL}$ and the intercept C, and then proceeds to Step ST44. It should be noted in the case of setting the right image as the standard image, the luminance parallax conversion unit 315 uses the luminance statistics information and the parallax statistics information to calculate Expressions (12) and (13), and determines the proportionality coefficient $K^{DfL}$ and the intercept C.

In Step ST44, the luminance parallax conversion unit 315 obtains the luminance value. The luminance parallax conversion unit 315 obtains the corrected luminance value PYC of the attention area from the attention area luminance correction unit 312, and then proceeds to Step ST45.

In Step ST45, the luminance parallax conversion unit 315 performs a conversion calculation. The luminance parallax conversion unit 315 uses the luminance value PYC obtained in Step ST44 and the proportionality coefficient $K^{DfL}$ and the intercept C obtained in Step ST43, thereby calculating Expression (9) to convert the luminance value PYC to the DfL parallax value $d^{DfL}$. The luminance parallax conversion unit 315 outputs the DfL parallax value $d^{DfL}$ obtained through the conversion calculation process to the stereo matching parallax estimation unit 32, and then proceeds to Step ST46.

In Step ST46, the luminance parallax conversion unit 315 determines whether the luminance parallax conversion is completed or not with respect to the attention area in the reference image. In the case where the luminance parallax conversion is not completed with respect to the attention area, the luminance parallax conversion unit 315 returns to Step ST44 to perform the process for the next process. Further, in the case where the luminance parallax conversion is completed with respect to the attention area, the luminance parallax conversion unit 315 terminates the luminance parallax conversion process with respect to the attention area in the standard image of the frame.

The stereo matching parallax estimation unit 32 uses the standard image and the reference image to perform the stereo matching parallax estimation by dynamic programming. Specifically, the stereo matching parallax estimation unit 32 sets a first matching area for each parallax estimation target position of the standard image. Further, the stereo matching parallax estimation unit 32 calculates a cost value that indicates a similarity between the first matching area and a second matching area of the reference image corresponding to the parallax value for each parallax value specified in advance. The stereo matching parallax estimation unit 32 sets a parallax value for which a sum of the cost values for an entire line becomes a minimum value with a highest similarity, as a parallax estimation result.

Figure 10A:
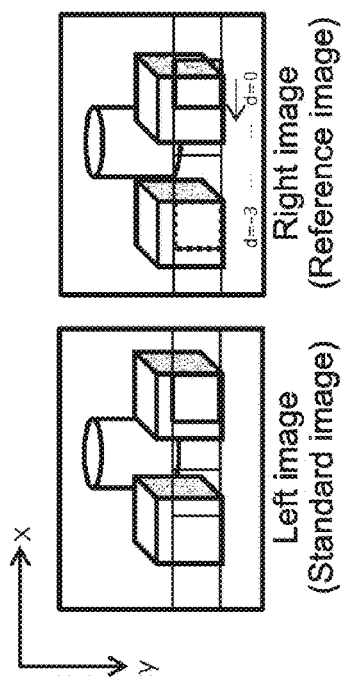
FIGS. 10A and 10B are diagrams for explaining an operation in the case where the parallax value with respect to a left image.
Figure 10B:
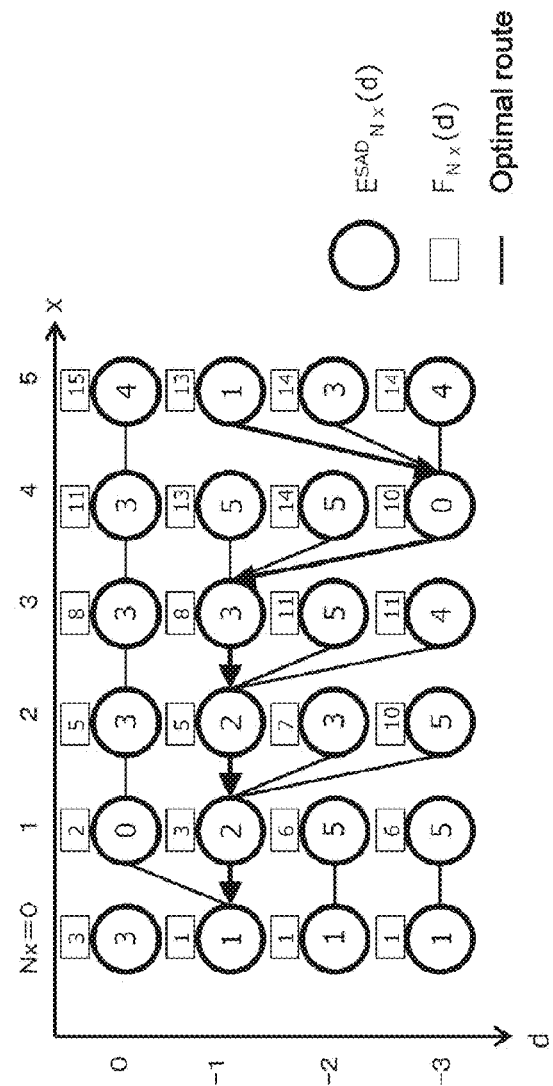

FIGS. 10A and 10B are diagrams for explaining an operation in the case where the parallax value with respect to the left image is obtained, with the left image as the standard image and the right image as the reference image. In DP matching parallax estimation, by setting, as a first matching area, a block having a predetermined size with a pixel on a parallax estimation target position in the standard image or the parallax estimation target position as a reference, a second matching area, which is a pixel corresponding thereto on the reference image or a block having the predetermined size, is searched for. Further, in the DP matching parallax estimation, in searching for the second matching area, a parallax value for which a sum of the cost values in an entire line becomes a minimum value with a highest similarity is determined by using the dynamic programming to be a parallax estimation result. It should be noted that, in the following description, the case where the DP matching parallax estimation on a pixel basis with the first matching area and the second matching area as one pixel size is exemplified, for ease of explanation.

As shown in FIG. 10A, the assumption is made that the size of one line as the X direction (horizontal direction) of an image is 6 pixels ($0 \leq Nx < 6$), and a parallax searching range dsr is 4 pixels ($-4 < dsr \leq 0$), for example.

In a general DP matching parallax estimation, a cost value $E_{Nx}(d)$ at a time when the parallax value d at a position on the standard image which is indicated by the coordinate value Nx is specified is defined as Expression (14).

$$E_{Nx}(d) = E^{SAD}_{Nx}(d) + W^{Spatial} E^{Spatial}(d) \quad (14)$$

$$E^{SAD}_{Nx}(d) = |PYS_{Nx} - PYR_{Nx+d}| \quad (15)$$

$$E^{Spatial}(d) = |d - d'| \quad (16)$$

In Expression (14), a sum of absolute differences $E^{SAD}_{Nx}(d)$ is a stereo matching result and is a cost value that indicates a similarity between the first matching area and the second matching area. Specifically, a similarity between a pixel at a position on the standard image which is indicated by the coordinate value Nx and a pixel at a position on the reference image which is indicated by a coordinate value Nx+d is indicated. The similarity is, specifically, a value calculated from Expression (15) in the case where the DP matching parallax estimation in the process on the pixel basis, with the sum of absolute differences (SAD) between the luminance values thereof as an indicator. It should be noted that a luminance value $PYS_{Nx}$ is a luminance value of the position on the standard image which is indicated by the coordinate value $N_X$, and a luminance value $PYR_{Nx+d}$ is a luminance value of the position on the reference image which is indicated by the coordinate value Nx+d.

Further, in Expression (14), $E^{Spatial}(d)$ indicates a cost value corresponding to a difference between the parallax value on a parallax estimation target position on the standard image and the parallax value on a preceding parallax estimation target position. As shown in Expression (16), $E^{Spatial}(d)$ is defined as an absolute difference between a parallax value d' ($-4 < d' \leq 0$) of a coordinate value $N_{X-1}$, which is the preceding estimation target position on the standard image and the parallax value d on the coordinate value Nx, which is the parallax estimation target position. It should be noted that $E^{Spatial}(d)$ is set as a space error cost value. $W^{Spatial}$ is a weight coefficient, and FIGS. 10A and 10B show the case of $W^{Spatial}=1$, as an example.

The cost value $E_{Nx}(d)$ calculated as described above is added for one-dimensional entire pixel line, that is, added from the positions of the coordinate values Nx=0 to SZx-1 (SZx: size in the X direction of the image, 6 pixels in FIG. 10), and a minimum sum thereof is set as a total sum of costs $E^{sum}$.

In the DP matching parallax estimation, when the total sum of costs $E^{sum}$ of the entire pixel line becomes a minimum value, by using the principle of optimality that the total sum of costs to the midway (Nx<5 (=SZx-1)) also has to be minimum, Expression (17) is efficiently calculated.

$$E^{sum} = \min_{d \in DS} \left( \sum_{Nx=0}^{SZ-1} E_{Nx}(d) \right) \quad (17)$$

For example, the minimum total sum of costs in the case of the coordinate value Nx and the parallax value d is represented by $F_{Nx}(d)$ expressed in Expression (18). By using a minimum total sum of costs $F_{Nx-1}$ to the coordinate value Nx-1 and the parallax value d' at the position of the coordinate value Nx-1 that gives a solution thereof, the minimum total sum of costs $F_{Nx}(d)$ is expressed by an recurrence formula in Expression (19). At this time, the parallax value d' that gives the minimum total sum of costs $F_{Nx}(d)$ is stored at all times as a parallax value $d^{pre}_{Nx}(d)$ expressed in Expression (20). Further, when the recurrence formula of Expression (19) is solved to a last column of the pixel line, the parallax value $d^{pre}_{Nx}(d)$ is traced back, thereby determining the parallax value of the entire line. It should be noted that in Expressions (18) to (20), "DS" indicates a set of the parallax values, and "d'" indicates an element of the set DS. In FIGS. 10A and 10B, "DS={0, -1, -2, -3}" is set. Further, in Expression (18), "q" indicates a value of the coordinate value Nx for calculating the minimum total sum of costs. For example, in the calculation of the minimum total sum of costs in the case of the coordinate value Nx of "3", "q=3" is determined, and a minimum value in the total sum of costs of the parallax value d' from the coordinate value Nx of "0" to "3" is obtained from Expression (18). Further, Expression (19) shows that "d'" is selected so that the inside the parenthesis on the right side is a minimum value, and the value in the parenthesis on the right side at this time is the minimum total sum of costs $F_{Nx}(d)$. Furthermore, Expression (20) indicates that "d'" is selected so that the inside the parenthesis on the right side is a minimum value, and the set of "d'" selected is the parallax value $d^{pre}_{Nx}(d)$.

$$F_{Nx}(d) = \min_{d' \in DS} \left( \sum_{Nx=0}^{q} E_{Nx}(d') \right) \quad (18)$$

$$F_{Nx}(d) = \min_{d' \in DS} (F_{Nx-1}(d') E_{Nx}(d')) \quad (19)$$

$$d^{pre}_{Nx}(d) = \operatorname*{argmin}_{d' \in DS} (F_{Nx-1}(d') + E_{Nx}(d)) \quad (20)$$

In FIG. 10B, numerical values in circles each indicate the sum of absolute differences $E^{SAD}_{Nx}(d)$ on the coordinate value Nx and the parallax value d, and numerical values in squares each indicate the minimum total sum of costs $F_{Nx}(d)$ on the coordinate value Nx and the parallax value d.

For example, in the case of the coordinate value Nx=0 and the parallax value d=0, the sum of absolute differences $E^{SAD}_{Nx}(d)=3$ and the minimum total sum of costs $F_{Nx}(d)=3$ are obtained. In the case of the coordinate value Nx=0 and the parallax value d=-1, the sum of absolute differences $E^{SAD}_{Nx}(d)=1$ and the minimum total sum of costs $F_{Nx}(d)=1$ are obtained. In the case of the coordinate value Nx=0 and the parallax value d=-2, the sum of absolute differences $E^{SAD}_{Nx}(d)=1$ and the minimum total sum of costs $F_{Nx}(d)=1$ are obtained. In the case of the coordinate value Nx=0 and the parallax value d=-3, the sum of absolute differences $E^{SAD}_{Nx}(d)=1$ and the minimum total sum of costs $F_{Nx}(d)=1$ are obtained.

Subsequently, in the case of the coordinate value Nx=1 and the parallax value d=0, the sum of absolute differences $E^{SAD}_{Nx}(d)=0$ is obtained, and in the case of a route from the coordinate value Nx=0 and the parallax value d=-1, the minimum total sum of costs $F_{Nx}(d)$ becomes a minimum value of "2". This route is set as an optimal route. It should be noted that there are a plurality of routes having the minimum value, a route in which a difference between the parallax value on the coordinate value Nx=0 and the parallax value on the coordinate value Nx=1 is the smallest is set as the optimal route.

In the case of the coordinate value Nx=1 and the parallax value d=−1, the sum of absolute differences $E^{SAD}Nx(d)=2$ is obtained, and in the case of a route from the coordinate value Nx=0 and the parallax value d=−1, the minimum total sum of costs FNx(d) becomes a minimum value of "3". This route is set as the optimal route. In the case of the coordinate value Nx=1 and the parallax value d=−2, the sum of absolute differences $E^{SAD}Nx(d)=5$ is obtained, and in the case of a route from the coordinate value Nx=0 and the parallax value d=−2, the minimum total sum of costs FNx(d) becomes a minimum value of "6". This route is set as the optimal route. In the same way, for each parallax on each position, the minimum total sum of costs FNx(d) and the optimal route are obtained.

Here, in the case of the coordinate value Nx=5 and the parallax value d=0, the sum of absolute differences $E^{SAD}Nx(d)=4$ is obtained, and in the case of a route from the coordinate value Nx=4 and the parallax value d=0, the minimum total sum of costs FNx(d) becomes a minimum value of "15". This route is set as the optimal route. In the case of the coordinate value Nx=5 and the parallax value d=−1, the sum of absolute differences $E^{SAD}Nx(d)=1$ is obtained, and in the case of a route from the coordinate value Nx=4 and the parallax value d=−3, the minimum total sum of costs FNx(d) becomes a minimum value of "13". This route is set as the optimal route. In the case of the coordinate value Nx=5 and the parallax value d=−2, the sum of absolute differences $E^{SAD}Nx(d)=3$ is obtained, and in the case of a route from the coordinate value Nx=4 and the parallax value d=−3, the minimum total sum of costs FNx(d) becomes a minimum value of "14". This route is set as the optimal route. In the case of the coordinate value Nx=5 and the parallax value d=−3, the sum of absolute differences $E^{SAD}Nx(d)=4$ is obtained, and in the case of a route from the coordinate value Nx=4 and the parallax value d=−3, the minimum total sum of costs FNx(d) becomes a minimum value of "14". This route is set as the optimal route.

That is, in FIG. 10B, at a time of the last column (Nx=5), in the case of the parallax value d=−1, the total sum of costs (F5(−1)=13) becomes a minimum value, and the parallax is traced back from the position of Nx=5 and d=−1, thereby determining an ultimate combination of the parallaxes d. Here, in the case of Nx=5, the optimal route on the parallax value d=−1 is a route continuing to the parallax value d=−3 on Nx=4. Further, in the case of Nx=4, the optimal route on the parallax value d=−3 is a route continuing to the parallax value d=−1 on Nx=3. In the case of Nx=3, the optimal route on the parallax value d=−1 is a route continuing to the parallax value d=−1 on Nx=2. In the case of Nx=2, the optimal route on the parallax value d=−1 is a route continuing to the parallax value d=−1 on Nx=1. In the case of Nx=1, the optimal route on the parallax value d=−1 is a route continuing to the parallax value d=−1 on Nx=0. Thus, the ultimate combination of the parallax values is determined to be "−1→−3→−1→−1→−1→−1" by tracing back the parallax value $d^{pre}Nx(d)$ as indicated by the arrows shown in FIG. 10B.

Although the DP matching parallax estimation in related art is carried out as described above, the stereo matching parallax estimation unit 32 performs calculation of a cost value including the parallax estimation result obtained by the attention area conversion processing unit 31. Specifically, as shown in Expression (21), the cost value is calculated so as to include a cost value (hereinafter, referred to as "procedure error cost value") $E^{DfL}Nx(d)$ corresponding to a difference between the parallax value specified in advance and DfL parallax value $d^{DfL}Nx$ obtained in the attention area conversion processing unit 31. As expressed in Expression (22), the procedure error cost value $E^{DfL}Nx$ is defined as an absolute difference between the specified parallax value d and the DfL parallax value $d^{DfL}Nx$ on the coordinate value Nx estimated by the attention area conversion processing unit 31.

$$E_{Nx}(d)=E^{SAD}{}_{Nx}(d)+W^{Spatial}E^{Spatial}(d)+W^{DfL}E^{DfL}{}_{Nx}(d) \qquad (21)$$

$$E^{DfL}{}_{Nx}(d)=|d-d^{DfL}{}_{Nx}| \qquad (22)$$

It should be noted that in the case where a pixel on the position of the coordinate value Nx on the standard image is a pixel which is outside of the attention area, for all the parallax values d, the procedure error cost value $E^{DfL}Nx(d)$ is set to "0". That is, outside of the attention area, the cost value which is the same as that in related art shown in Expression (14) is provided. Further, in Expression (21), $W^{DfL}$ represents a weight coefficient.

Figure 11A:
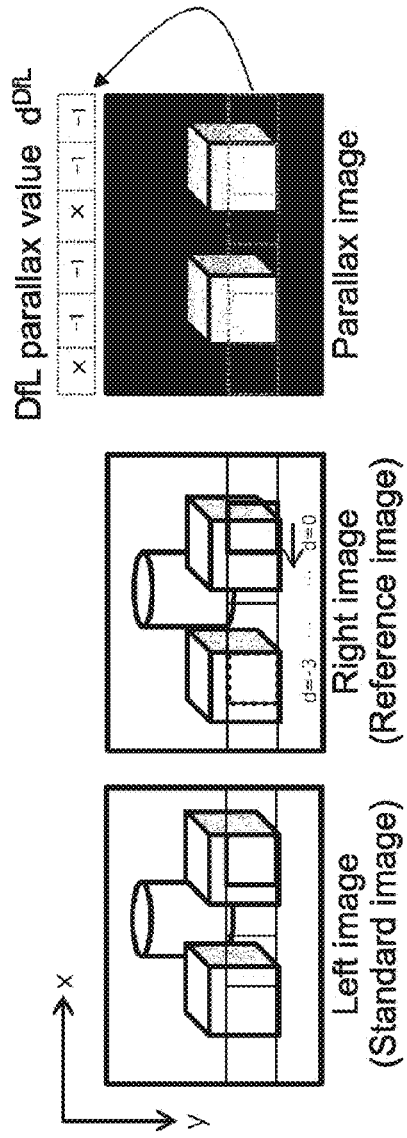
FIGS. 11A and 11B are diagrams for explaining an operation in the case where the parallax value with respect to a left image by using a conversion result of the attention area conversion processing unit.
Figure 11B:
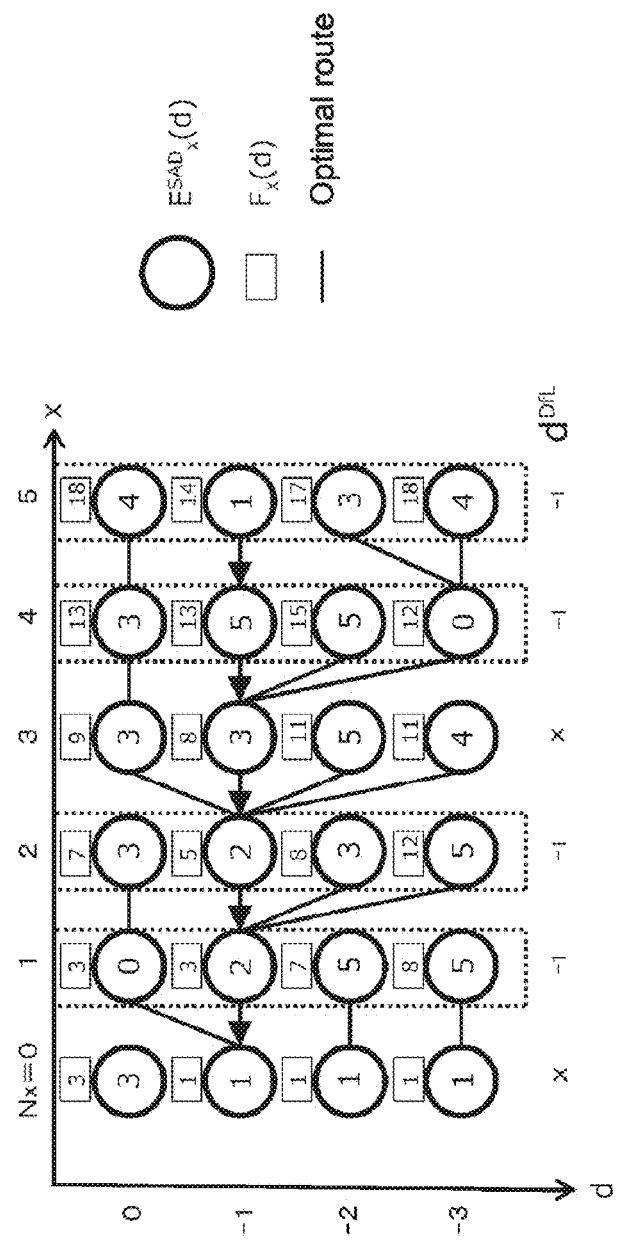

FIGS. 11A and 11B are diagrams for explaining the operation in the case where the parallax value with respect to the left image is obtained by using the estimation result of the attention area conversion processing unit. It should be noted that the same condition as in FIGS. 10A and 10B is applied to FIGS. 11A and 11B, so the sum of absolute differences $E^{SAD}Nx(d)$ as the stereo matching result is not changed.

In FIG. 11(A), the parallax image is an image that indicates the parallax value obtained by performing the luminance parallax conversion from the standard image. For example, the DfL parallax value $d^{DfL}$ obtained by the luminance parallax conversion with two cubes set as the attention area is exemplified by a numerical value of the parallax image. It should be noted that a symbol "x" in the figures represents a pixel with no DfL parallax value because of the outside of the attention area. In FIGS. 11A and 11B, pixels on the positions of coordinate values Nx=1, 2, 4, and 5 are attention pixels, and the weight coefficient is $W^{spatial}=W^{DfL}=1$.

The procedure error cost value $E^{DfL}$ corresponding to the difference with the luminance parallax conversion value is added, with the result that changes in the optimal route and the minimum total sum of costs FNx(d) shown in FIGS. 10 and 11 are caused.

In FIG. 11B, numerical values in circles each indicate the sum of absolute differences $E^{SAD}Nx(d)$ on the coordinate value Nx and the parallax value d, and numerical values in squares each indicate the minimum total sum of costs FNx(d) on the coordinate value Nx and the parallax value d.

For example, in the case of the coordinate value Nx=0 and the parallax value d=0, the sum of absolute differences $E^{SAD}Nx(d)=3$ and the minimum total sum of costs FNx(d)=3 are obtained. In the case of the coordinate value Nx=0 and the parallax value d=−1, the sum of absolute differences $E^{SAD}Nx(d)=1$ and the minimum total sum of costs FNx(d)=1 are obtained. In the case of the coordinate value Nx=0 and the parallax value d=−2, the sum of absolute differences $E^{SAD}Nx(d)=1$ and the minimum total sum of costs FNx(d)=1 are obtained. In the case of the coordinate value Nx=0 and the parallax value d=−3, the sum of absolute differences $E^{SAD}Nx(d)=1$ and the minimum total sum of costs FNx(d)=1 are obtained.

Next, in the case of the coordinate value Nx=1 and the parallax value d=0, the sum of absolute differences $E^{SAD}Nx(d)=0$ is obtained, and in the case of a route from the coordinate value Nx=0 and the parallax value d=−1, the minimum total sum of costs FNx(d) becomes a minimum value of "3". This route is set as an optimal route. In the case of the coordinate value Nx=1 and the parallax value d=−1, the sum of absolute differences $E^{SAD}Nx(d)=2$ is obtained, and in the case of a route from the coordinate value Nx=0 and the parallax value d=−1, the minimum total sum of costs FNx(d) becomes a minimum value of "3". This route is set as the optimal route. In the case of the coordinate value Nx=1 and the parallax value d=−2, the sum of absolute differences $E^{SAD}Nx(d)=5$ is obtained, and in the case of a route from the coordinate value Nx=0 and the parallax value d=−2, the minimum total sum of costs FNx(d) becomes a minimum value of "7". This route is set as the optimal route. In the same way, for each parallax on each position, the minimum total sum of costs FNx(d) and the optimal route are obtained.

Here, in the case of the coordinate value Nx=5 and the parallax value d=0, the sum of absolute differences $E^{SAD}Nx(d)=4$ is obtained, and in the case of a route from the coordinate value Nx=4 and the parallax value d=0, the minimum total sum of costs FNx(d) becomes a minimum value of "18". This route is set as the optimal route. In the case of the coordinate value Nx=5 and the parallax value d=−1, the sum of absolute differences $E^{SAD}Nx(d)=1$ is obtained, and in the case of a route from the coordinate value Nx=4 and the parallax value d=−1, the minimum total sum of costs FNx(d) becomes a minimum value of "14". This route is set as the optimal route. In the case of the coordinate value Nx=5 and the parallax value d=−2, the sum of absolute differences $E^{SAD}Nx(d)=3$ is obtained, and in the case of a route from the coordinate value Nx=4 and the parallax value d=−3, the minimum total sum of costs FNx(d) becomes a minimum value of "17". This route is set as the optimal route. In the case of the coordinate value Nx=5 and the parallax value d=−3, the sum of absolute differences $E^{SAD}Nx(d)=4$ is obtained, and in the case of a route from the coordinate value Nx=4 and the parallax value d=−3, the minimum total sum of costs FNx(d) becomes a minimum value of "18". This route is set as the optimal route.

That is, in FIG. 11B, at a time of the last column (Nx=5), in the case of the parallax value d=−1, the total sum of costs (F5(−1)=14) becomes a minimum value, and the parallax is traced back from the position of Nx=5 and d=−1, thereby determining an ultimate combination of the parallaxes d. Here, in the case of Nx=5, the optimal route on the parallax value d=−1 is a route continuing to the parallax value d=−1 on Nx=4. Further, in the case of Nx=4, the optimal route on the parallax value d=−1 is a route continuing to the parallax value d=−1 on Nx=3. In the case of Nx=3, the optimal route on the parallax value d=−1 is a route continuing to the parallax value d=−1 on Nx=2. In the case of Nx=2, the optimal route on the parallax value d=−1 is a route continuing to the parallax value d=−1 on Nx=1. In the case of Nx=1, the optimal route on the parallax value d=−1 is a route continuing to the parallax value d=−1 on Nx=0. Thus, the ultimate combination of the parallax values D is determined to be "−1→−1→−1→−1→−1→−1" by tracing back the parallax value $d^{pre}Nx(d)$ as indicated by the arrows shown in FIG. 11B. That is, the parallax values D indicated by the parallax information output from the stereo matching parallax estimation unit 32 is determined to be "−1, −1, −1, −1, −1, −1" in the case of FIG. 11A.

In the general stereo matching method, there is a fear that it may be impossible to obtain the corresponding points or the corresponding areas with high accuracy in an area with less pattern or an area in which the same pattern is repeated. For example, in the area with less pattern (area with less variation in luminance), approximately the same sum of absolute differences $E^{SAD}(d)$ is obtained with respect to any parallax values d. Therefore, if a noise or the like is superimposed on an image signal, a correct result is difficult to be obtained. In FIGS. 10A and 10B, the pixel on the position of the coordinate value Nx=4 on the standard image and the pixel on the position of the coordinate value Nx=1 on the reference image have the same pattern, so the value of the sum of absolute differences $E^{SAD}4(-3)$ becomes small. That is, an error correspondence of the stereo matching is caused, and thus an error parallax value is determined.

In the DP matching parallax estimation, in Expression (14), the second term on the right side is a term that works so as to have a parallax value close to the parallax estimation result of the next pixel, so even if error stereo matching is performed, the term works so as to correct the error. However, when a large error or continuous errors are caused in an area for which the stereo matching method does not work well, such as the area with less pattern or the area where the same pattern is repeated, there is a fear that it may be impossible to correct the error even by the DP matching parallax estimation, and consequently an error parallax value may be calculated.

In view of this, in the present technology, in the attention area, by calculating the cost value with the procedure error cost value $E^{DfL}$ included, it is possible to calculate the cost value that indicates the correspondence condition of the images with higher accuracy even in the area for which the stereo matching does not work well, such as the area with less pattern or the area where the same pattern is repeated. Thus, according to the present technology, it is possible to prevent the error correspondence of the stereo matching which is difficult to be corrected by the stereo matching in related art and perform correct parallax estimation with high accuracy, for example.

It should be noted that in FIGS. 10 and 11, the DP matching parallax estimation on the pixel basis is exemplified. However, the DP matching parallax estimation may be performed on a block basis with a parallax estimation target position of the standard image as a reference. The DP matching parallax estimation is performed on the block basis is less affected by a noise or the like as compared to the case of the DP matching parallax estimation on the pixel basis. Therefore, by performing the DP matching parallax estimation on the block basis, it is possible to perform more robust parallax estimation as compared to the case where the DP matching parallax estimation on the pixel basis.

Figure 12:
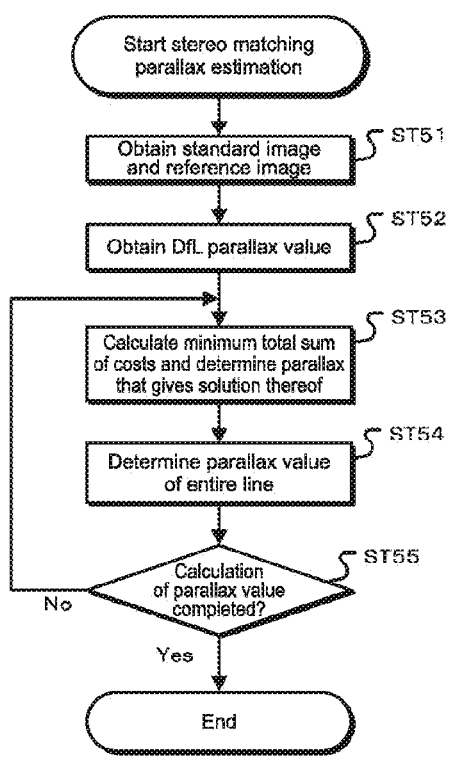
FIG. 12 is a flowchart showing an example of a stereo matching parallax estimation unit.

FIG. 12 is a flowchart showing an example of the operation of a stereo matching parallax estimation unit. In Step ST51, the stereo matching parallax estimation unit 32 obtains the standard image and the reference image. For example, the stereo matching parallax estimation unit 32 obtains image signals of the left image and the right image with the left image as the standard image and the right image as the reference image and then proceeds to Step ST52.

In Step ST52, the stereo matching parallax estimation unit 32 obtains the DfL parallax value. The stereo matching parallax estimation unit 32 obtains the DfL parallax value generated by the attention area conversion processing unit 31 and then proceeds to Step ST53.

In Step ST53, the stereo matching parallax estimation unit 32 performs calculation of a minimum total sum of costs and determination of a parallax that gives a solution thereof. The stereo matching parallax estimation unit 32 calculates Expressions (15) to (22) described above to obtain the minimum total sum of costs and a parallax on a preceding position which gives the solution, and then proceeds to Step ST54. Further, the DfL parallax value $d^{D/L}$ by the luminance parallax conversion is not obtained with respect to pixels outside the attention area. Therefore, the stereo matching parallax estimation unit 32 sets the procedure error cost value $E^{D/L}$ to "0" with respect to the pixels outside the attention area and calculates the total sum of costs on the basis of a detection result of the attention area detection unit 311.

In Step ST54, the stereo matching parallax estimation unit 32 determines the parallax value of the entire line. The stereo matching parallax estimation unit 32 performs tracing back from the parallax that the total sum of costs is a minimum value in the last column, determines the parallax value of the entire line, and then proceeds to Step ST55.

In Step ST55, the stereo matching parallax estimation unit 32 determines whether the calculation of the parallax value is completed for each pixel of the standard image. If there is a pixel line for which the parallax value is not calculated in the standard image, the stereo matching parallax estimation unit 32 returns to Step ST53. Further, if there is no pixel line for which the parallax value is not calculated, the stereo matching parallax estimation unit 32 terminates the parallax estimation with respect to the standard image and then performs the parallax estimation for a new standard image.

It should be noted that in the above, the example is described in which the stereo matching result of determining the correspondence in the right image is obtained with the left image as the standard image. Similarly, however, a correspondence in the left image may be determined with the right image as the standard image.

As described above, according to the present technology, the luminance value is converted into the parallax value in the attention area on the standard image, and the search for the optimal route and the calculation of the cost value are performed with the parallax value included. Thus, even in the area where there is no pattern or the area where the same pattern is repeated, it is possible to perform more robust parallax estimation as compared to the stereo matching method.

In addition, in the luminance parallax conversion in the attention area, from the DP matching parallax estimation result of the preceding frame, the square root of the luminance value and the proportionality coefficient of the parallax value in Expression (9) are determined. Therefore, in a head frame, there is a possibility that an error may be generated in the parallax estimation result in the area for which the stereo matching method does not work well. Therefore, in performing the luminance parallax estimation, the second frame is affected by the DP matching parallax estimation accuracy. However, as defined in Expressions (10) to (13), the maximum parallax value and the minimum parallax value in the attention area are calculated, thereby making it possible to be less affected by the error parallax estimation result. Further, as the frame is advanced, even in an area where an error is caused in the stereo matching parallax estimation, by the combination with the parallax estimation by the luminance parallax conversion, the parallax can be obtained correctly. As a result, the accuracy of deriving the proportionality coefficient in Expression (9) is improved, with the result that the parallax estimation in the attention area can be performed with high accuracy.

<4. Other Operations of Image Processing Apparatus>

In the operation described above, for example, the luminance value and the color difference value are each compared with the threshold value, and on the basis of the comparison result, the area having the common desired quality in the image is detected as the attention area. However, the threshold value may not be a predetermined value but may be dynamically set by analyzing the distribution of the color difference components of the image. For example, from a preceding frame, a histogram or the like of the color difference component is created, and a threshold value for extracting an image area of a desired subject may be adjusted on the basis of the histogram or the like.

Further, in the above operation, for example, the luminance value and the color difference value are each compared with the threshold value, and on the basis of the comparison result, the area having the desired quality in the image is detected as the attention area. However, the attention area may be detected by another method. For example, an edge or a line may be extracted from the image, and the edge or the line extracted may be traced, thereby dividing the area. In addition, a texture analysis is performed with respect to the image, and an area with a texture exhibiting a desired characteristic may be set as the attention area. In this way, by performing the texture analysis, it is possible to detect the attention area in the case where there is a small difference in the luminance or color.

Furthermore, in the operation described above, the luminance parallax conversion characteristic is estimated on the basis of the maximum luminance value and the minimum luminance value after the correction in the attention area. However, if a noise is superimposed on the image in the attention area, there is a fear that the maximum luminance value and the minimum luminance value have different values from the luminance of the desired subject, and the luminance parallax conversion characteristic is difficult to be estimated with high accuracy. For this reason, the maximum luminance value and the minimum luminance value may be determined on the basis of the distribution of the luminance values. For example, as shown in Expression (23), by using the average luminance value PYCavg and a statistic value σPYC that indicates the distribution, the maximum luminance value and the minimum luminance value may be determined. Further, in the same way, for the parallax information, as shown in Expression (24), by using the average parallax value Davg and a statistic value σD, the maximum parallax value Dmax and the minimum parallax value Dmin may be determined. As a result, it is possible to perform more robust luminance parallax conversion with respect to an error in the stereo matching parallax estimation or a noise included in the standard image.

$$PYC_{max} = PYC_{avg} + \sigma_{PYC}, PYC_{min} = PYC_{avg} - \sigma_{PYC} \qquad (23)$$

$$D_{max} = D_{avg} + \sigma_D, D_{min} = D_{avg} - \sigma_D \qquad (24)$$

As the statistic value σPYC that indicates the distribution, a standard deviation or the like of the corrected luminance value PYC in the attention area can be used. Further, as the statistic value σD that indicates the distribution in Expression (24), a standard deviation or the like of the parallax value D can be used.

The estimation of the proportionality coefficient $K^{D/L}$ and the intercept C may be performed by using a plurality of past frames. For example, the proportionality coefficients $K^{D/L}$ and the intercepts C of a predetermined number of frames of the past from the frame for which the parallax estimation is performed are stored, and on the basis of changes in the proportionality coefficients $K^{DfL}$ and the intercepts C stored, the proportionality coefficient $K^{DfL}$ and the intercept C corresponding to the frame for which the parallax estimation is performed are predicted. By using a prediction result, the luminance parallax conversion may be performed.

Figure 13:
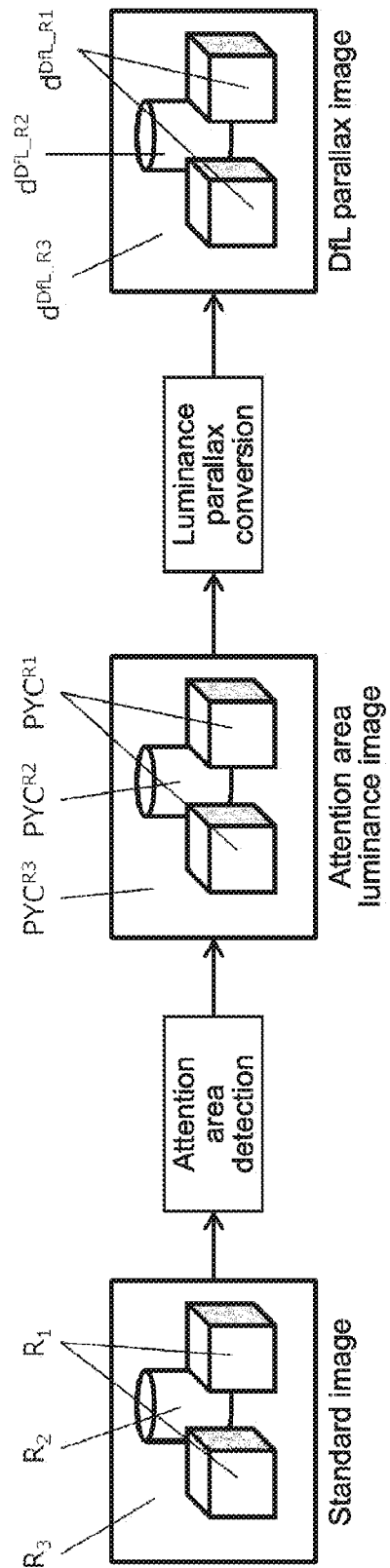
FIG. 13 is a diagram for explaining the case where a plurality of attention areas are provided.

The number of attention areas may not be limited to one, but a plurality of attention areas may be provided in the image. For example, as shown in FIG. 13, a plurality of attention areas Rn (n=1, 2, 3) are provided, a proportionality coefficient $K^{DfL\_Rn}$ and an intercept $C^{Rn}$ in Expression (25) are determined for each attention area, and a corrected luminance value $PYC^{Rn}$ in each of the attention area may be converted to a DfL parallax value $d^{DfL\_Rn}$.

$$d^{DfL\_Rn} = K^{DfL\_Rn}\sqrt{PYC^{Rn}} + C^{Rn} \quad (25)$$

Further, in the case where the value of the proportionality coefficient $K^{DfL}$ in Expression (9) or (25) is apparently wrong, the luminance parallax conversion may not be performed. For example, in the case where a slope indicated by the proportionality coefficient $K^{DfL}$ is too steep or too gentle as compared to a preset range, it is determined that the proportionality coefficient $K^{DfL}$ is wrong, and the luminance parallax conversion is not performed. Through this process, it is possible to more reliably prevent an error luminance parallax conversion from being performed.

Further, outside the attention area, the luminance parallax conversion unit 315 may set the DfL parallax value $d^{DfL}$ to an identification value indicating the outside of the attention area, and in the case where the DfL parallax value $d^{DfL}$ is the identification value, the stereo matching parallax estimation unit 32 may set the procedure error cost value $E^{DfLNx}(d)$ to "0". In this case, it is possible to perform the parallax estimation of the present technology without supplying the detection result of the attention area from the attention area conversion processing unit 31 to the stereo matching parallax estimation unit 32.

The series of processes described in the specification can be executed by hardware, software, or a composite structure of those. When the processes are performed by the software, a program in which a process sequence is recorded is installed in a memory in a computer incorporated in dedicated hardware and is executed. Alternatively, the program can be installed in a general-purpose computer that can execute various processes and executed.

For example, the program can be recorded in a hard disk or a ROM (read only memory) as a recording medium in advance. Alternatively, the program can be temporarily or permanently stored (recorded) in a removable recording medium such as a flexible disk, a CD-ROM (compact disc read only memory), an MO (magneto optical) disk, a DVD (digital versatile disc), a magnetic disk, and a semiconductor memory card. The removable recording medium can be provided as so-called package software. Further, in addition to installing to a computer from the removable recording medium, the program may be transferred to a computer in a wireless or wired manner via a network such as a LAN (local area network) and the Internet from a download site. The computer can receive the program transferred in the way mentioned above and install in a recording medium such as a hard disk therein.

As described above, according to the present technology, in the stereo matching parallax estimation, for the image area with small pattern variation or small luminance value variation or the image area where the same pattern is repeated, for which the estimation is difficult to be performed, the cost value is calculated by using the DfL parallax value. Thus, by determining the parallax value on the basis of the cost value calculated, it is possible to obtain the parallax estimation result more robustly with higher accuracy as compared to the technology in related art.

In addition, in the depth distance estimation method that uses the characteristic that the illuminance of light is attenuated in inverse proportion to the square of the distance in related art, in order to obtain a parallax value between stereo images from an estimated depth distance, it is necessary to perform a calibration in advance based on a light reflection characteristic of an image pickup target object or a measurement result of a light source. Further, an absolute distance is necessary. However, according to the present technology, from the luminance value of the past frame and the parallax estimation result, the relationship between the luminance value and the parallax value can be calculated, so it is unnecessary to perform the calibration in advance. Further, the parallax estimation can be performed without using the absolute distance.

In addition, the area to which the DfL parallax estimation is applied is limited, and the stereo matching parallax estimation method of related art is applied to the other area. In this case, even if a plurality of subjects with different reflection characteristics are included in an image, by performing the parallax estimation as described above for the attention area set for each subject, it is possible to perform the parallax estimation for each subject with high accuracy without measuring the reflection characteristics or the like of the subjects in advance.

It should be understood by those skilled in the art that various modifications, combinations, sub-combinations and alterations may occur depending on design requirements and other factors insofar as they are within the scope of the appended claims or the equivalents thereof.

It should be noted that the present disclosure can take the following configurations.

(1) An image processing apparatus, including:
an attention area detection unit configured to detect an attention area including a desired subject from a standard image;
a luminance parallax conversion unit configured to perform a luminance parallax conversion with respect to the attention area on the basis of a luminance parallax conversion characteristic estimated by using a past frame; and
a parallax estimation unit configured to perform parallax estimation on the basis of the standard image and a reference image, a viewpoint position of which is different from that of the standard image, and perform, in the attention area, the parallax estimation by using a luminance parallax conversion result obtained by the luminance parallax conversion unit.

(2) The image processing apparatus according to Item (1), in which
the luminance parallax conversion unit performs the luminance parallax conversion by using a luminance value of the attention area, the luminance value of the attention area being corrected in accordance with a depth distance to the desired subject.

(3) The image processing apparatus according to Item (2), in which
the luminance parallax conversion unit estimates a proportionality coefficient and an intercept on an assumption that a square root of the luminance value corrected in accordance with the depth distance is proportional to a parallax value in the estimation of the luminance parallax conversion characteristic.

(4) The image processing apparatus according to Item (3), in which the luminance parallax conversion unit estimates the luminance parallax conversion characteristic on the basis of a maximum luminance value, a minimum luminance value, a maximum parallax value, and a minimum parallax value in the attention area of the past frame.

(5) The image processing apparatus according to Item (4), in which the luminance parallax conversion unit calculates the maximum luminance value and the minimum luminance value on the basis of a distribution of the luminance values and an average value of the luminance values in the attention area, and calculates the maximum parallax value and the minimum parallax value on the basis of a distribution of the parallax values and an average value of the parallax values in the attention area.

(6) The image processing apparatus according to any one of Items (1) to (5), in which the parallax estimation unit sets a first matching area for each parallax estimation target position of the standard image, calculates a cost value that indicates a similarity between the first matching area and a second matching area corresponding to each parallax value in the reference image for each parallax value specified in advance, and sets the parallax value, for which a total sum of the cost values of a line is a minimum value with a highest similarity, as a parallax estimation result for each line.

(7) The image processing apparatus according to Item (6), in which the parallax estimation unit causes, in the cost value, a cost value corresponding to a difference between the specified parallax value and the parallax value obtained by the luminance parallax conversion by the luminance parallax conversion unit to be included, in the attention area detected by the attention area detection unit.

(8) The image processing apparatus according to Item (7), in which the parallax estimation unit calculates the cost value without the difference being obtained, in an area excluding the attention area detected by the attention area detection unit.

(9) The image processing apparatus according to any one of Items (6) to (8), in which the parallax estimation unit causes a cost value corresponding to a difference between the parallax value of the parallax estimation target position and the parallax value of a preceding parallax estimation target position in the standard image to be included.

(10) The image processing apparatus according to any one of Items (1) to (9), in which the parallax estimation unit uses dynamic programming in the parallax estimation.

(11) The image processing apparatus according to any one of Items (1) to (10), in which the attention area detection unit compares a color difference value and a luminance value of the standard image with predetermined threshold values to detect the attention area.

(12) The image processing apparatus according to any one of Items (1) to (11), in which the attention area detection unit performs a texture analysis with respect to the standard image to detect the attention area.

By the image processing apparatus, the image processing method, and the program according to the present technology, with respect to the attention area detected from the standard image, the luminance parallax conversion characteristic is estimated from the luminance value of the attention area of the past frame and the parallax estimation result, and the luminance parallax conversion is performed for the attention area on the basis of the estimation result. Further, the parallax estimation is performed which is based on the similarity between the standard image and the reference image the viewpoint position of which is different from that of the standard image, and the similarity is calculated by using the luminance parallax conversion result with respect to the attention area. That is, in the attention area, not only the similarity between the standard image and the reference image but also the luminance parallax conversion result is used to perform the parallax estimation, with the result that, even in the case where the attention area is the image for which the parallax estimation is difficult to be performed on the basis of the similarity, it is possible to perform the parallax estimation with high accuracy from the plurality of images with different viewpoint positions. Thus, this is suitable for a system that uses stereo images obtained by a stereo video camera, a stereo endoscope, or the like.

What is claimed is:

1. A medical device, comprising:
circuitry configured to
detect, from a standard medical image signal, an area including a subject in a standard medical image represented by the standard medical image signal; and
determine a disparity between the standard medical image and a reference medical image based on:
a result of the detecting of the area,
the standard medical image signal,
a reference medical image signal representing the reference medical image, and
a past medical image signal generated before generating the standard medical image signal,
wherein the standard medical image and the reference medical image have different viewpoint positions.

2. The medical device according to claim 1, wherein the standard medical image includes an inner wall surface inside a body or an organ as the subject.

3. The medical device according to claim 2, wherein the circuitry is configured to detect the area based on predetermined color information regarding the inner wall surface inside the body or the organ.

4. The medical device according to claim 1, wherein the standard medical image is captured by an endoscope.

5. The medical device according to claim 1, wherein the circuitry is configured to perform, on the area in the standard medical image, a luminance conversion based on luminance information of the standard medical image signal and luminance information of the past medical image signal.

6. The medical device according to claim 5, wherein the circuitry is configured to perform the luminance conversion by using a luminance value of the area, the luminance value of the area being corrected in accordance with a depth distance to the subject.

7. The medical device according to claim 6, wherein the circuitry is configured to estimate a proportionality coefficient and an intercept on an assumption that a square root of the luminance value corrected in accordance with the depth distance is proportional to a parallax value in an estimation of a luminance conversion characteristic.

8. The medical device according to claim 7, wherein the circuitry is configured to estimate the luminance conversion characteristic on the basis of a maximum luminance value, a minimum luminance value, a maximum parallax value, and a minimum parallax value in the area of the past medical image.

9. The medical device according to claim 8, wherein the circuitry is configured to calculate the maximum luminance value and the minimum luminance value based on a distribution of the luminance values and an average value of the luminance values in the area, and calculate the maximum parallax value and the minimum parallax value on the basis of a distribution of the parallax values and an average value of the parallax values in the area.

10. The medical device according to claim 1, wherein the circuitry is configured to use dynamic programming in the determining of the disparity.

11. The medical device according to claim 1, wherein the circuitry is configured to compare a color difference value and a luminance value of the standard medical image with predetermined threshold values to detect the area.

12. The medical device according to claim 1, wherein the circuitry is configured to perform a texture analysis with respect to the standard medical image to detect the area.

13. An image processing apparatus, comprising:
circuitry configured to
  detect, from a standard image signal, an area including a subject in a standard image represented by the standard image signal; and
  determine a disparity between the standard image and a reference image based on:
    a result of the detecting of the area,
    the standard image signal,
    a reference image signal representing the reference image, and
    a past image signal generated before generating the standard image signal,
  wherein the standard image and the reference image have different viewpoint positions.

14. The image processing apparatus according to claim 13, wherein
the circuitry is configured to perform, on the area in the standard medical image, a luminance conversion based on luminance information of the standard image signal and luminance information of the past image signal.

15. The image processing apparatus according to claim 14, wherein
the circuitry is configured to perform the luminance conversion by using a luminance value of the area, the luminance value of the area being corrected in accordance with a depth distance to the subject.

16. The image processing apparatus according to claim 13, wherein
the circuitry is configured to use dynamic programming in the determining of the disparity.

17. The image processing apparatus according to claim 13, wherein
the circuitry is configured to compare a color difference value and a luminance value of the standard image with predetermined threshold values to detect the area.

18. The image processing apparatus according to claim 13, wherein
the circuitry is configured to perform a texture analysis with respect to the standard image to detect the area.

19. An image processing method, comprising:
detecting, from a standard image signal, an area including a subject in a standard image represented by the standard image signal; and
determining a disparity between the standard image and a reference image based on:
  a result of the detecting of the area, the standard image signal,
  a reference image signal representing the reference image, and
  a past image signal generated before generating the standard image signal,
wherein the standard image and the reference image have different viewpoint positions.

20. A non-transitory computer readable medium having stored thereon instructions, which, when executed, perform a method comprising:
detecting, from a standard image signal, an area including a subject in a standard image represented by the standard image signal; and
determining a disparity between the standard image and a reference image based on:
  a result of the detecting of the area,
  the standard image signal,
  a reference image signal representing the reference image, and
  a past image signal generated before generating the standard image signal,
wherein the standard image and the reference image have different viewpoint positions.

* * * * *